(12) United States Patent
Modi et al.

(10) Patent No.: US 10,149,984 B2
(45) Date of Patent: Dec. 11, 2018

(54) DEVICE AND METHOD FOR SKIN LASER TREATMENT

(75) Inventors: Stefano Modi, Borgo San Lorenzo (IT);
Maurizio Scortecci, Prato (IT);
Damiano Fortuna, Rignano sull'Arno (IT); Tiziano Zingoni, Florence (IT);
Leonardo Masotti, Sesto Fiorentino (IT); Gabriele Clementi, Florence (IT);
Nicola Zerbinati, Pavia (IT)

(73) Assignee: EL.EN. S.P.A., Calenzano Firenze (IT)

(*) Notice: Subject to any disclaimer, the term of this patent is extended or adjusted under 35 U.S.C. 154(b) by 1008 days.

(21) Appl. No.: 13/984,635

(22) PCT Filed: Feb. 9, 2012

(86) PCT No.: PCT/IB2012/000233
§ 371 (c)(1),
(2), (4) Date: Oct. 2, 2013

(87) PCT Pub. No.: WO2012/107830
PCT Pub. Date: Aug. 16, 2012

(65) Prior Publication Data
US 2014/0018783 A1    Jan. 16, 2014

(30) Foreign Application Priority Data

Feb. 11, 2011  (IT) .............................. FI2011A0023

(51) Int. Cl.
*A61N 5/06* (2006.01)
*A61B 18/20* (2006.01)
(Continued)

(52) U.S. Cl.
CPC ............ *A61N 5/0616* (2013.01); *A61B 18/12* (2013.01); *A61B 18/203* (2013.01);
(Continued)

(58) Field of Classification Search
CPC ...... A61N 5/0616; A61N 1/0472; A61N 1/06; A61N 1/328; A61B 18/12; A61B 18/203;
(Continued)

(56) References Cited

U.S. PATENT DOCUMENTS

| 6,702,808 B1* | 3/2004 | Kreindel | ................ A61B 18/14 128/898 |
| 6,997,923 B2 | 2/2006 | Anderson et al. | |

(Continued)

FOREIGN PATENT DOCUMENTS

| JP | 2008-500846 A | 1/2008 |
| JP | 2010-528803 A | 8/2010 |

(Continued)

OTHER PUBLICATIONS

Japanese Office Action dated Nov. 18, 2015.
(Continued)

*Primary Examiner* — Gary Jackson
*Assistant Examiner* — Jessandra Hough
(74) *Attorney, Agent, or Firm* — McGlew and Tuttle, P.C.

(57) ABSTRACT

The system for treating a region of the epidermis, comprising: —at least one laser energy source; —a time control device to generate a laser beam; —a laser energy focusing system arranged and produced to direct a laser beam on said region of the epidermis. The control device generates a laser beam comprising a plurality of composite pulses, emitted at a base frequency, each composite pulse comprising a sequence of sub-pulses at a higher frequency than said base frequency.

36 Claims, 20 Drawing Sheets

(51) Int. Cl.
- A61N 1/04 (2006.01)
- A61N 1/06 (2006.01)
- A61N 1/32 (2006.01)
- A61B 18/12 (2006.01)
- A61B 17/00 (2006.01)
- A61B 18/00 (2006.01)
- A61B 90/50 (2016.01)

(52) U.S. Cl.
CPC .............. *A61N 1/0472* (2013.01); *A61N 1/06* (2013.01); *A61N 1/328* (2013.01); *A61B 90/50* (2016.02); *A61B 2017/00172* (2013.01); *A61B 2018/0047* (2013.01); *A61B 2018/2035* (2013.01); *A61B 2018/20359* (2017.05)

(58) Field of Classification Search
CPC .......... A61B 90/50; A61B 2017/00172; A61B 2018/0047; A61B 2018/2035; A61B 2018/2095; A61B 18/20359
See application file for complete search history.

(56) References Cited

U.S. PATENT DOCUMENTS

| | | | | |
|---|---|---|---|---|
| 2008/0058782 | A1* | 3/2008 | Frangineas | A61B 18/203 606/9 |
| 2009/0093799 | A1 | 4/2009 | Davenport et al. | |
| 2010/0174277 | A1 | 7/2010 | Bernabei | |
| 2011/0077627 | A1* | 3/2011 | Lemberg | A61B 18/203 606/11 |
| 2012/0097833 | A1* | 4/2012 | Lin | G02B 13/0005 250/201.1 |

FOREIGN PATENT DOCUMENTS

| | | | |
|---|---|---|---|
| WO | 02/26147 A1 | 4/2002 | |
| WO | 2005/099369 A2 | 10/2005 | |
| WO | 2007/099460 A2 | 9/2007 | |
| WO | 2008/035012 A2 | 3/2008 | |
| WO | 2008/152630 A2 | 12/2008 | |
| WO | 2009/052847 A1 | 4/2009 | |
| WO | 2009/104178 A2 | 8/2009 | |
| WO | WO2009104178 A2 * | 8/2009 | ............... A61N 5/00 |
| WO | WO2010150175 A1 * | 10/2010 | ............... A61N 5/06 |
| WO | 2010/150175 A1 | 12/2010 | |

OTHER PUBLICATIONS

Chernoff G, Slatkine M, Zair And, Mead D., SilkTouch: a new technology for skin resurfacing in aesthetic surgery, in J Clin Laser Med Surg. Apr. 1995;13(2):97-100.

Waldorf HA, Kauvar AN, Geronemus RG, Skin resurfacing of fine to deep rhytides using a char-free carbon dioxide laser in 47 patients, in Dermatol Surg. Nov. 1995;21 (11):940-6.

David LM, Same AJ, Unger WP., Rapid laser scanning for facial resurfacing, in Dermatol Surg. Dec. 1995;21 (12):1031-3.

Lask G, Keller G, Lowe N, Gormley D., Laser skin resurfacing with the SilkTouch flashscanner for facial rhytides, in Dermatol Surg. Dec. 1995;21(12):1021-4.

Apfelberg DB., Ultrapulse carbon dioxide laser with CPG scanner for full-face resurfacing for rhytids, photoaging, and acne scars, in Plast Reconstr Surg. Jun. 1997;99(7):1817-25.

Apfelberg DB, Smoller B., UltraPulse carbon dioxide laser with CPG scanner for deepithelialization: clinical and histologic study, in Plast Reconstr Surg. Jun. 1997;99(7):2089-94.

Raulin C, Drommer RB, Schonermark MP, Werner S., Facial wrinkles—ultrapulsed C02 laser: alternative or supplement to surgical face lift?, in Laryngorhinootologie. Jun. 1997;76(6):351-7.

Trelles MA, Rigau J, Mellor TK, Garcia L., A clinical and histological comparison of flashscanning versus pulsed technology in carbon dioxide laser facial skin resurfacing, in Dermatol Surg. Jan. 1998;24(I):43-9.

Weinstein C, Computerized scanning erbium:YAG laser for skin resurfacing, in Dermatol Surg. Jan. 1998;24(I):83-9.

Bernstein LJ, Kauvar AN, Grossman MC, Geronemus RG., Scar resurfacing with high-energy, short-pulsed and flashscanning carbon dioxide lasers, in Dermatol Surg. Jan. 1998;24(I):101-7.

Vaïsse V, Clerici T, Fusade T., "Bowen disease treated with scanned pulsed high energy CO2 laser. Follow-up of 6 cases", in Ann. Dermatol. Venereol. Nov. 2001;128(II):1220-4.

Toshio Ohshiro et al., Laser Dermatology—State of the Art, proceedings of the 7th Congress International Society for Laser Surgery and Medicine in Connection with Laser 87 Optoelectronics, ed. Springer-Verlag, 1988, p. 513 ff.

Fitzpatrick RE, Rostan EF, Marchell N., Collagen tightening induced by carbon dioxide laser versus erbium: YAG laser, in Lasers Surg. Med. 2000;27(5):395-403.

Hasegawa T, Matsukura T, Mizuno Y, Suga Y, Ogawa H, Ikeda S., Clinical trial of a laser device called fractional photothermolysis system for acne scars, in Dermatol. Sep. 2006;33(9):623-7.

Rahman Z, Alam M, Dover JS., Fractional Laser treatment for pigmentation and texture improvement, in Skin Therapy Lett. Nov. 2006; 11(9): 7-11.

Laubach H, Chan HH, Rius F, Anderson RR, Manstein D., Effects of skin temperature on lesion size in fractional photothermolysis, in Lasers Surg Med. Jan. 2007;39(I):14-8.

Collawn SS., Fraxel skin resurfacing, in Ann Plast Surg. Mar. 2007;58(3):237-40.

Hantash BM, Bedi VP, Chan KF, Zachary CB., Ex vivo histological characterization of a novel ablative fractional resurfacing device, in Lasers Surg Med. Feb. 2007;39(2):87-95.

Hantash BM, Bedi VP, Kapadia B, Rahman Z, Jiang K, Tanner H, Chan KF, In vivo histological evaluation of a hovel ablative fractional resurfacing device, in Lasers Surg Med. Feb. 2007;39(2):96-107.

Goldberg DJ, Fazeli A, Berlin AL., Clinical, laboratory, and MRI analysis of cellulite treatment with a unipolar radiofrequency device, in Dermatol Surg. Feb. 2008;34(2):204-9.

Montesi G, Calvieri S, Balzani A, Gold MH., Bipolar radiofrequency in the treatment of dermatologic imperfections: clinicopathological and immunohistochemical aspects, in J.Drugs Dermatol. Feb. 2007;6(2):212-5.

Green HA, Domankevitz Y, Nishoka NS. Pulsed carbon dioxide laser ablation of burned skin: in vitro and in vivo analysis. Laser Surg Med. 1990;10(5):476-84.

* cited by examiner

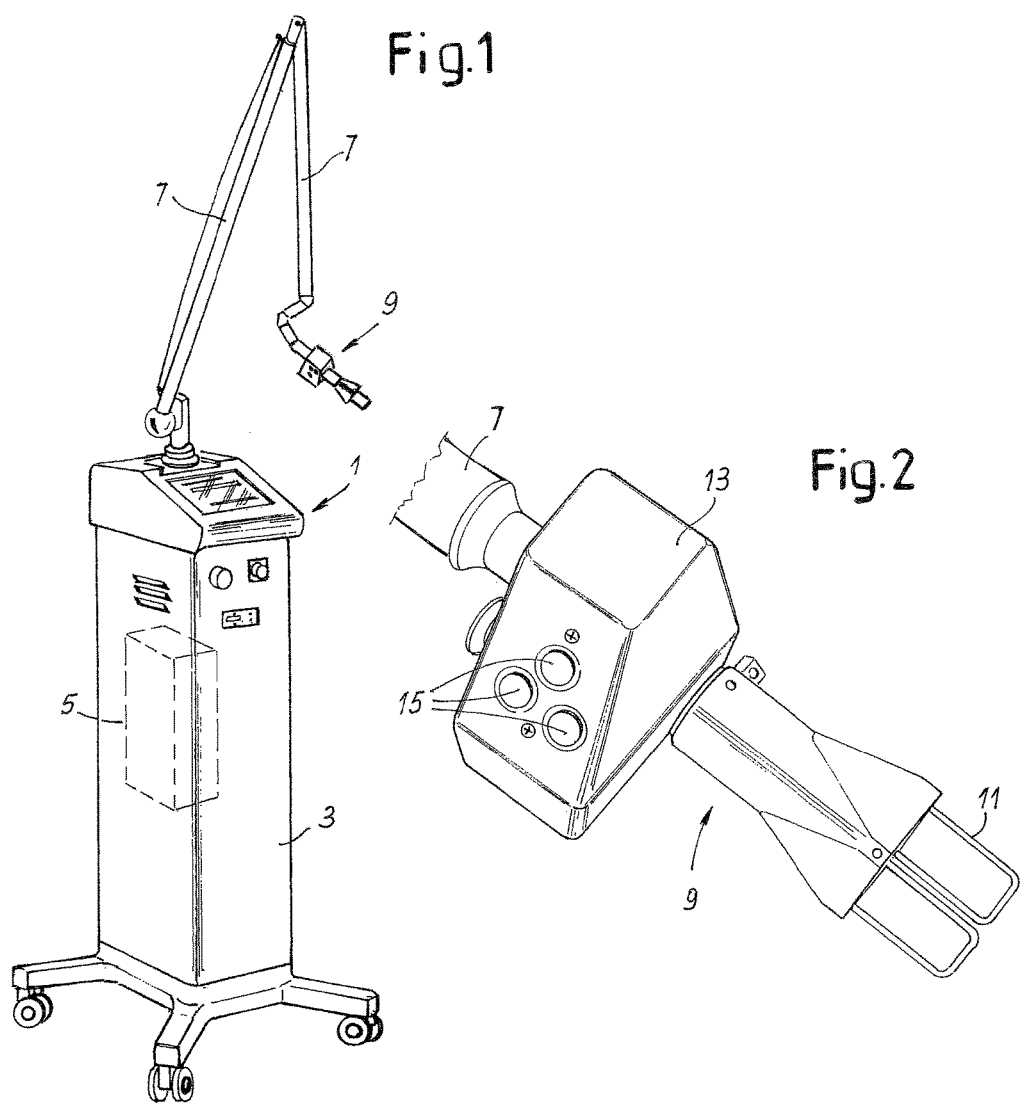

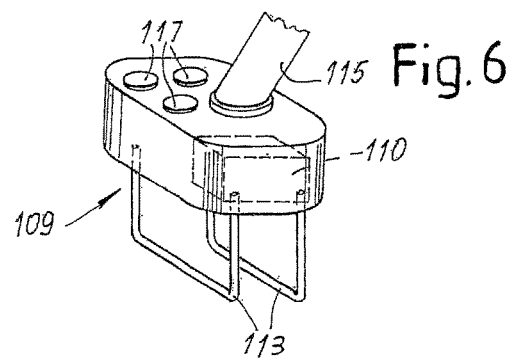
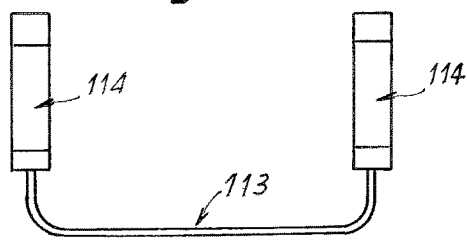
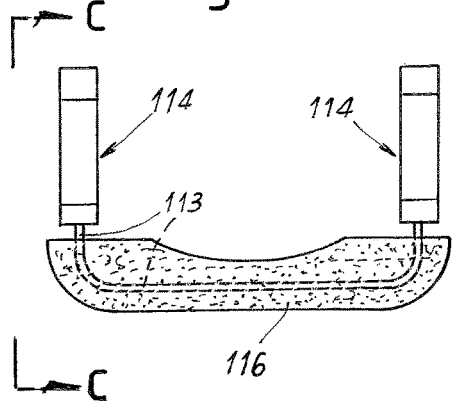
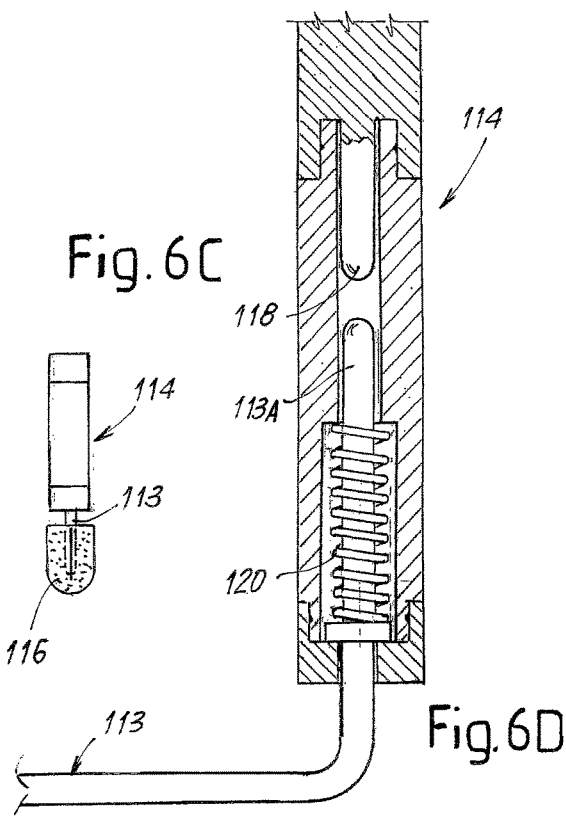

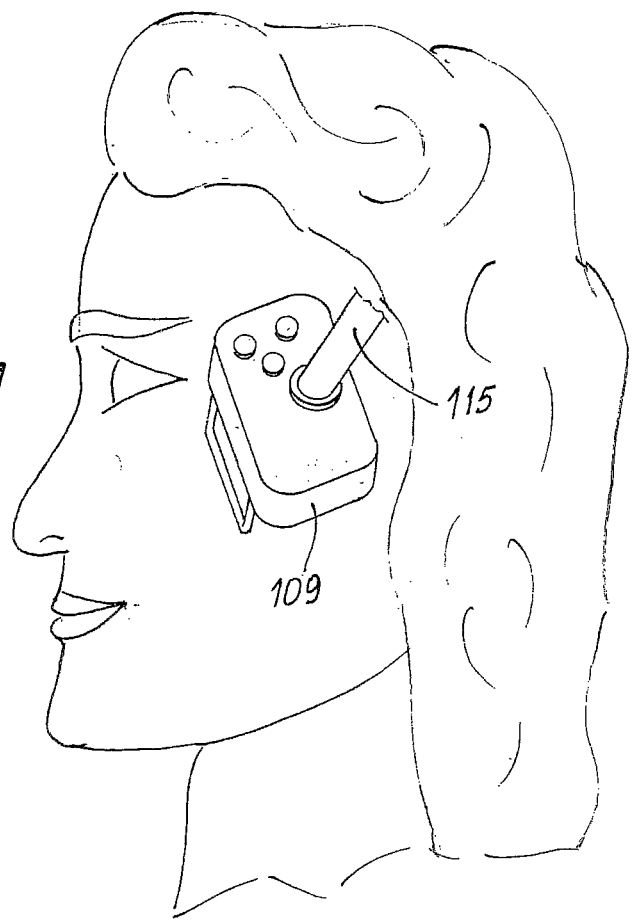

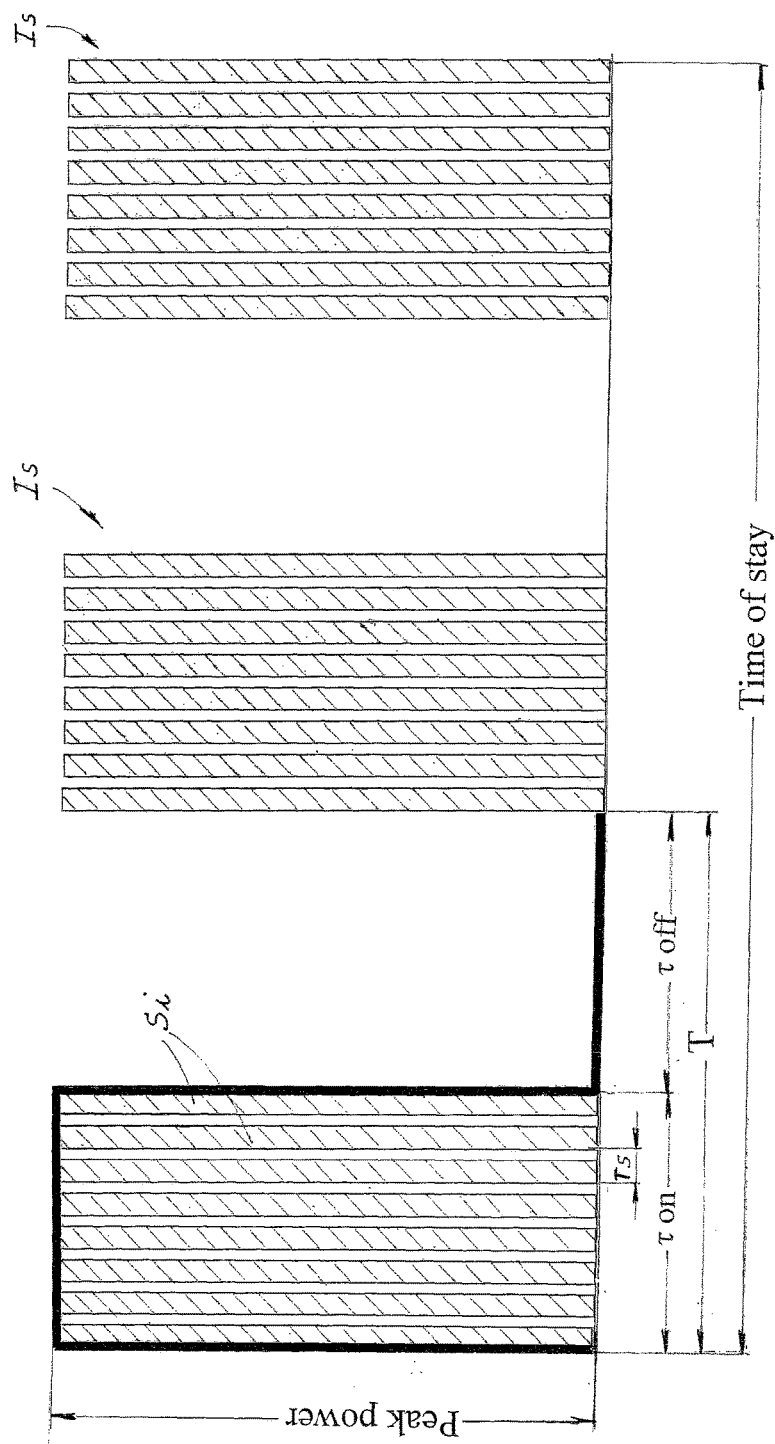

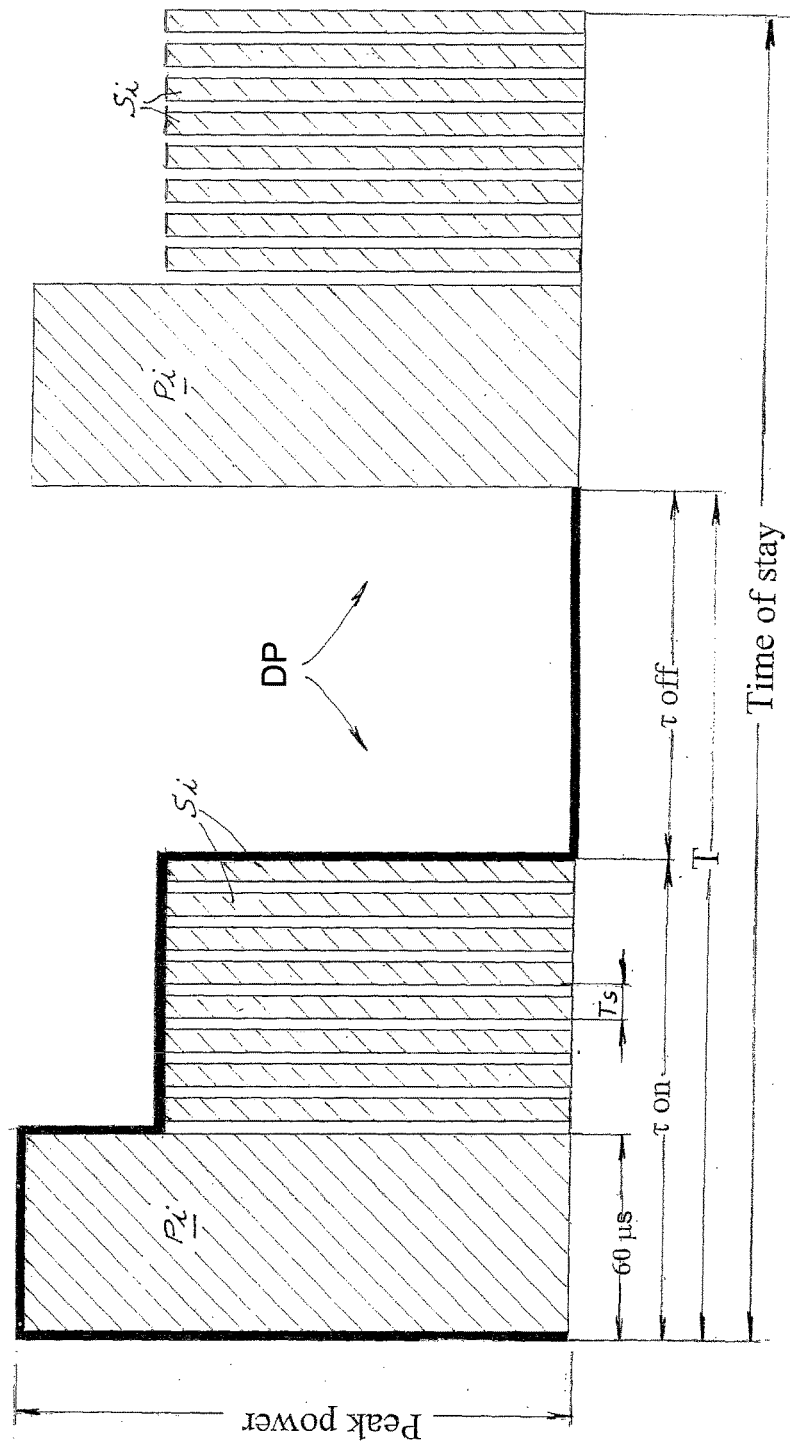

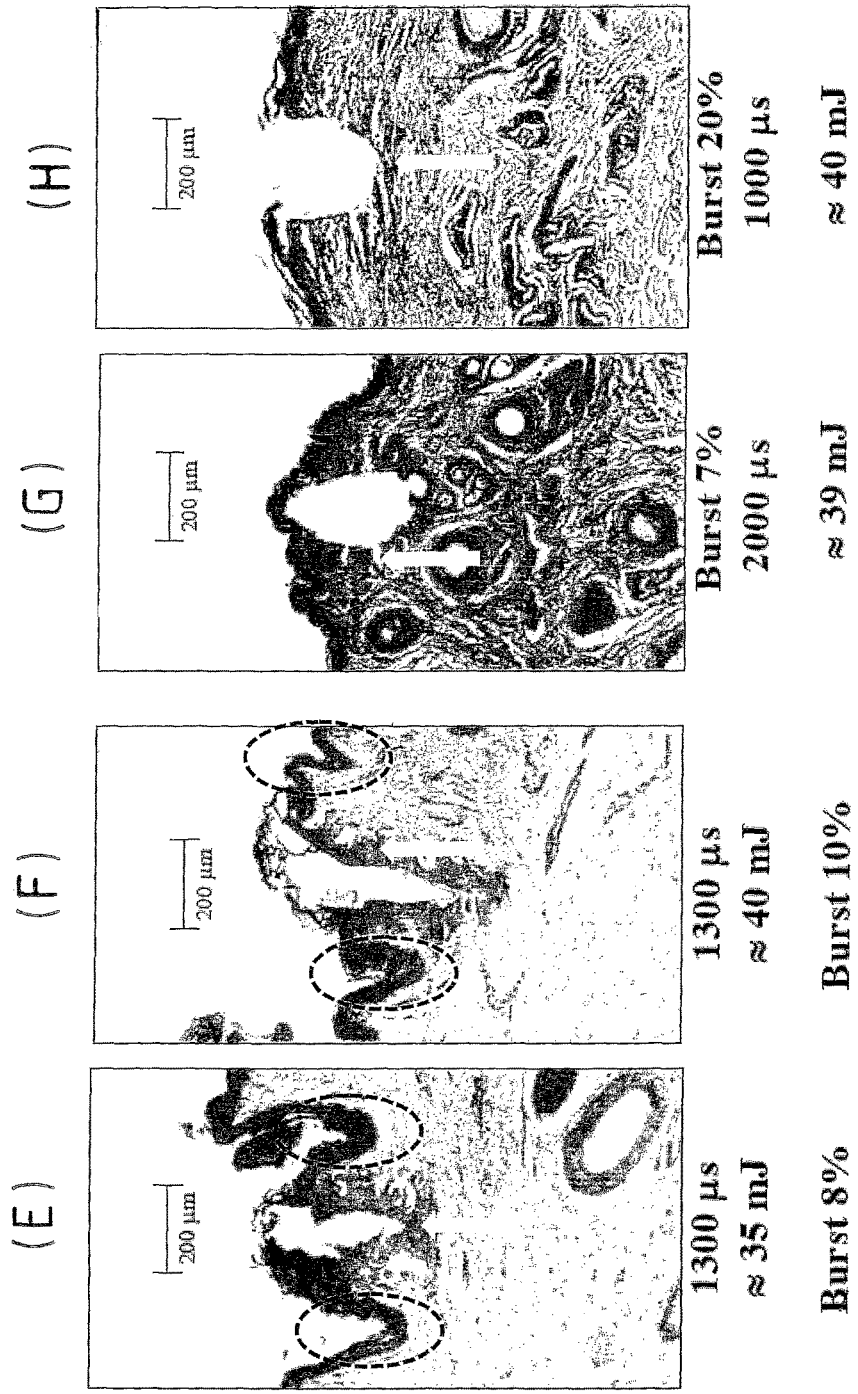

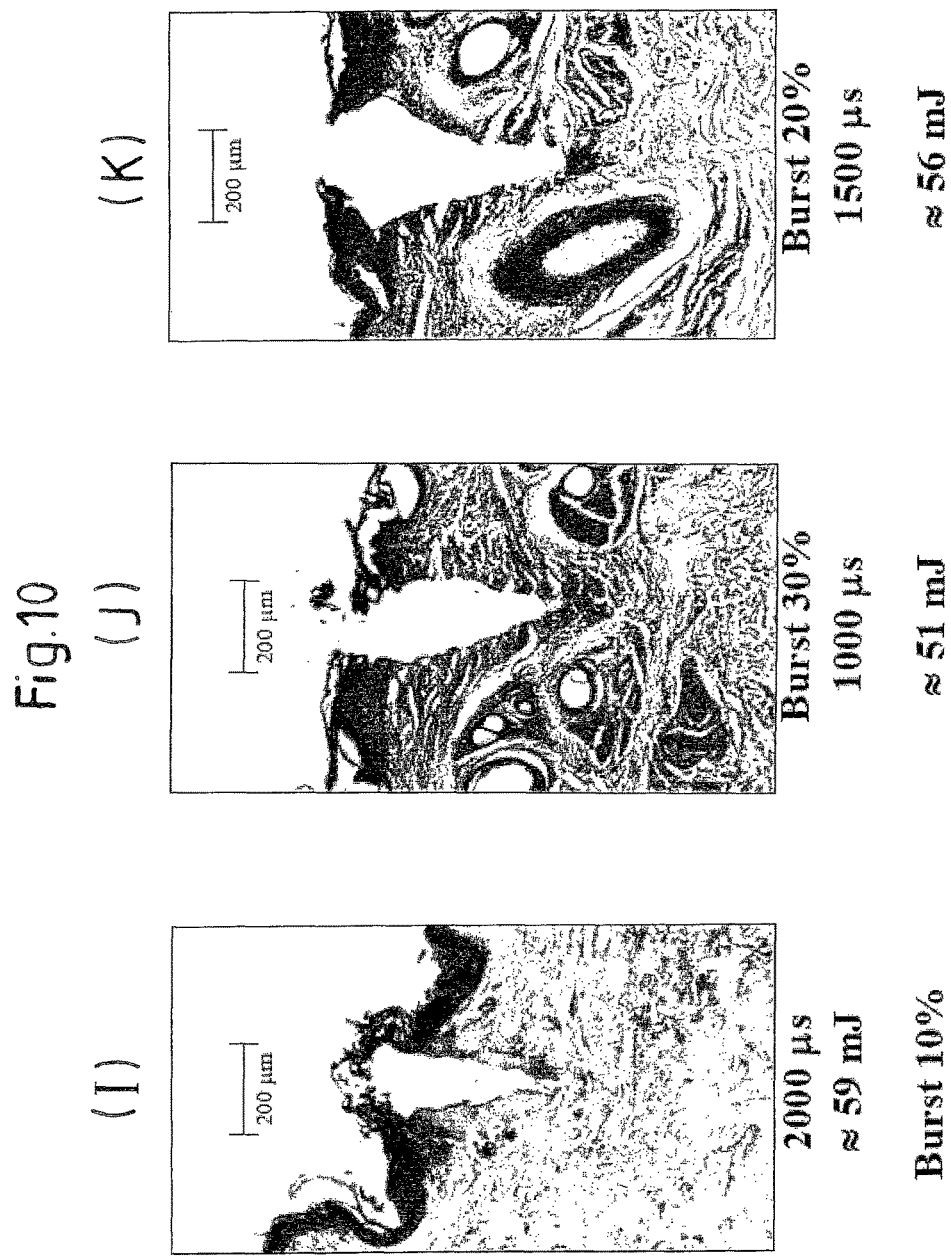

Fig. 11
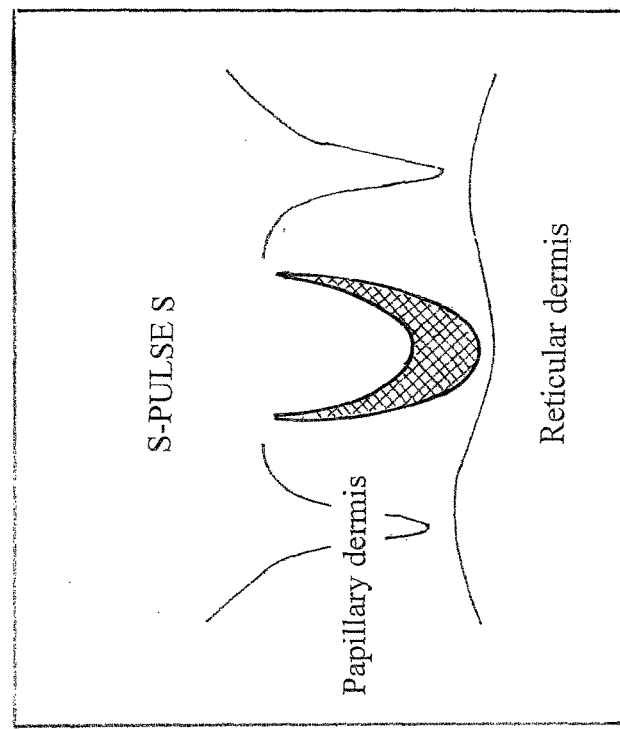
(A)
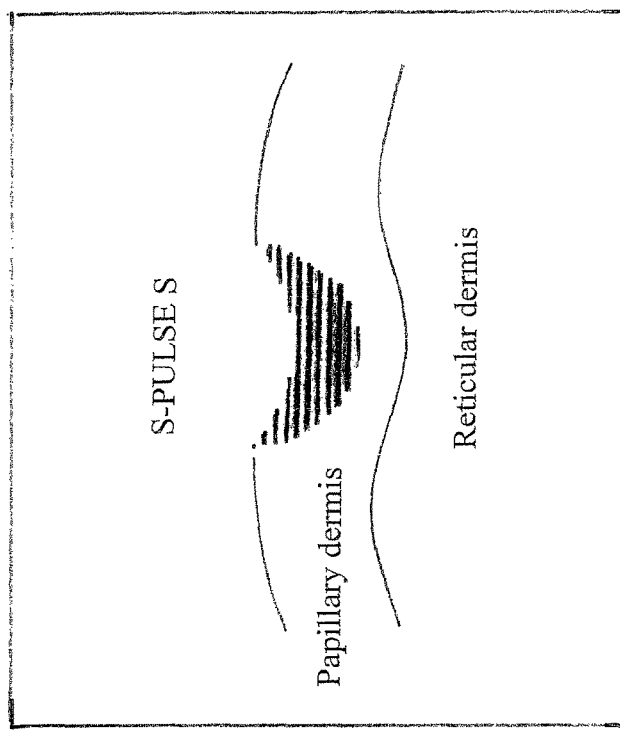
(B)

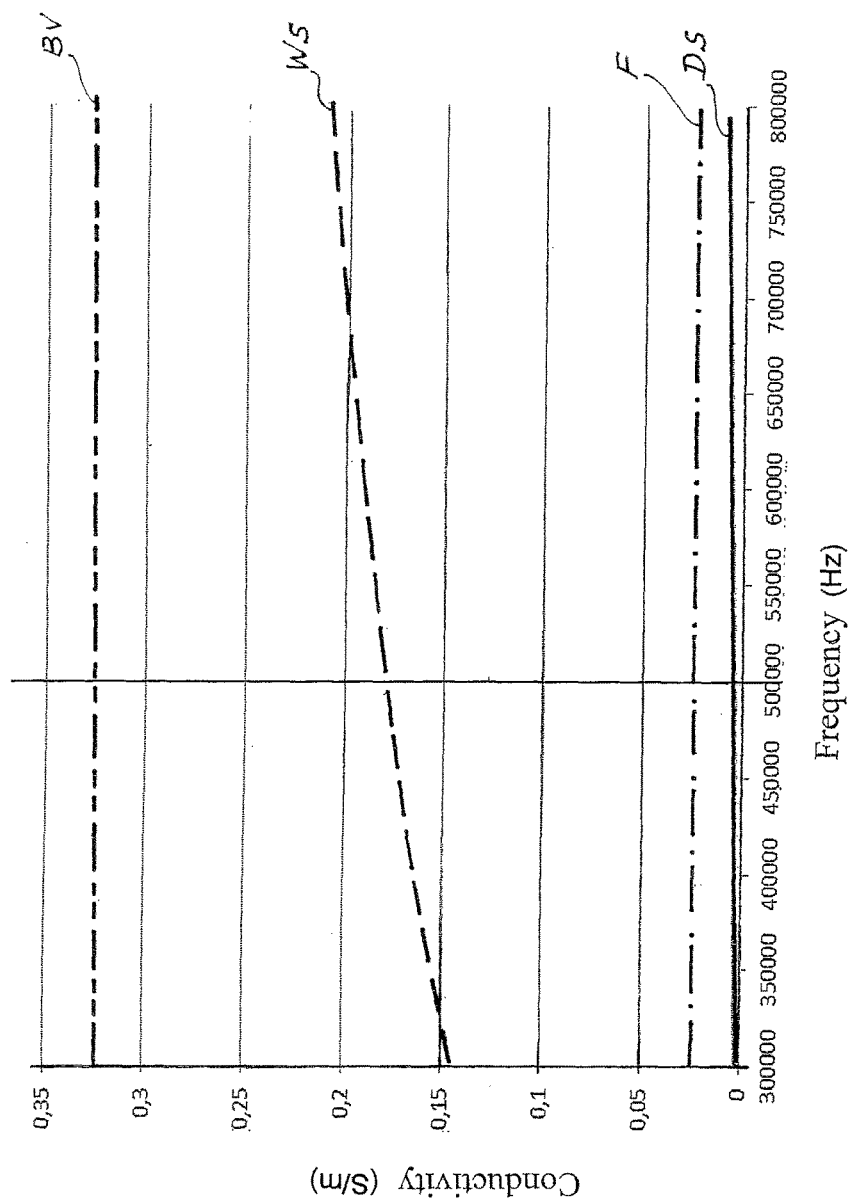

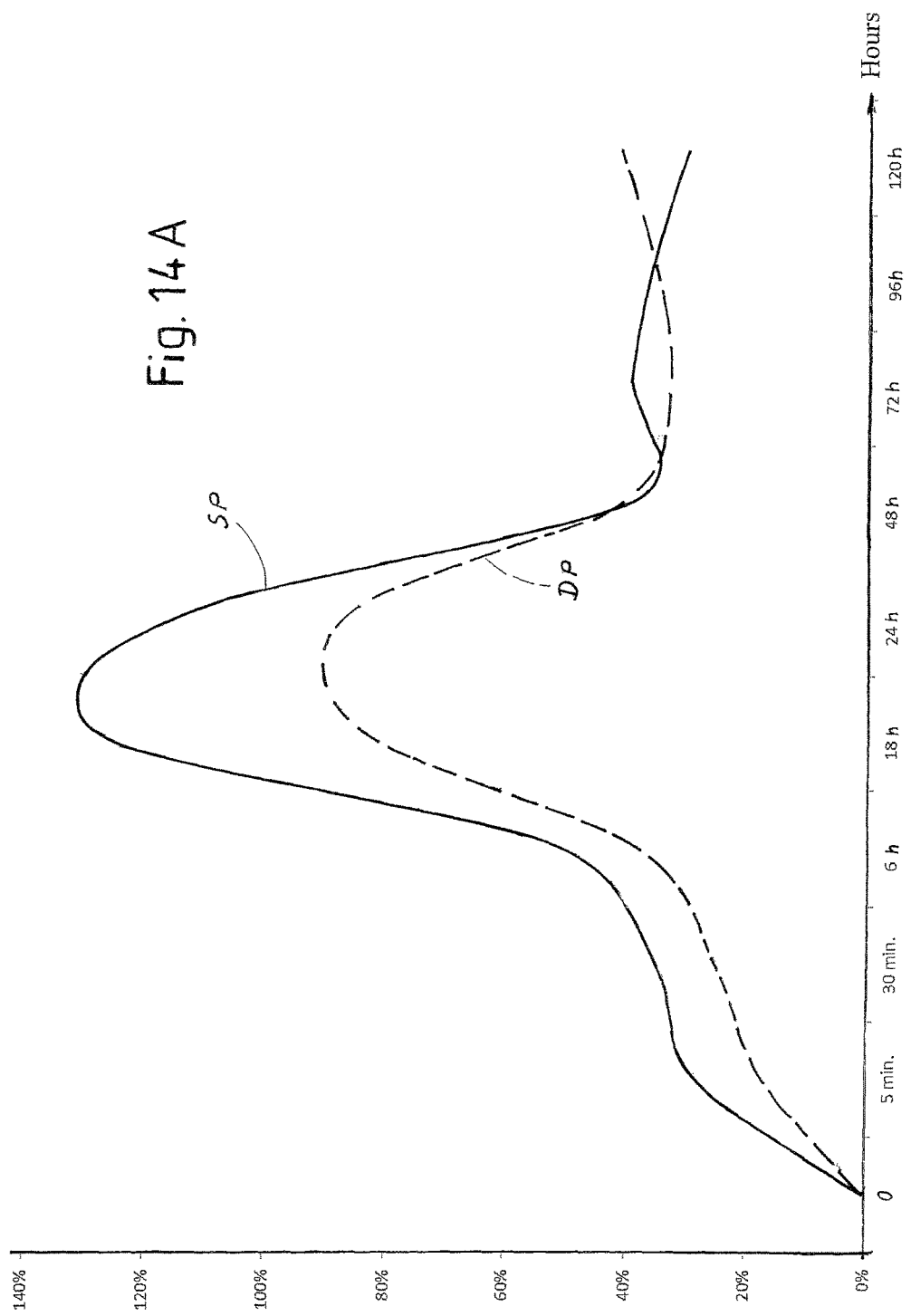

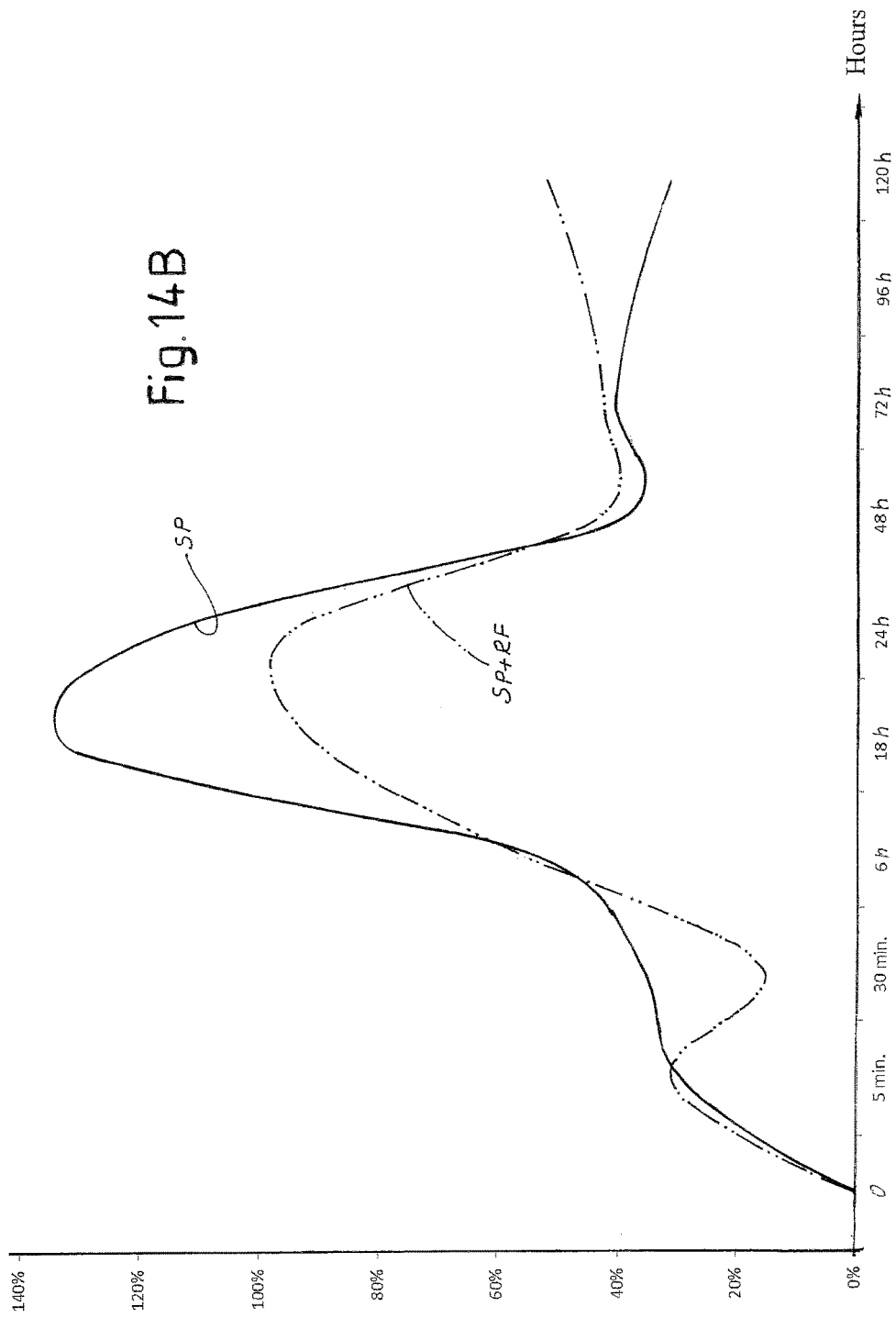

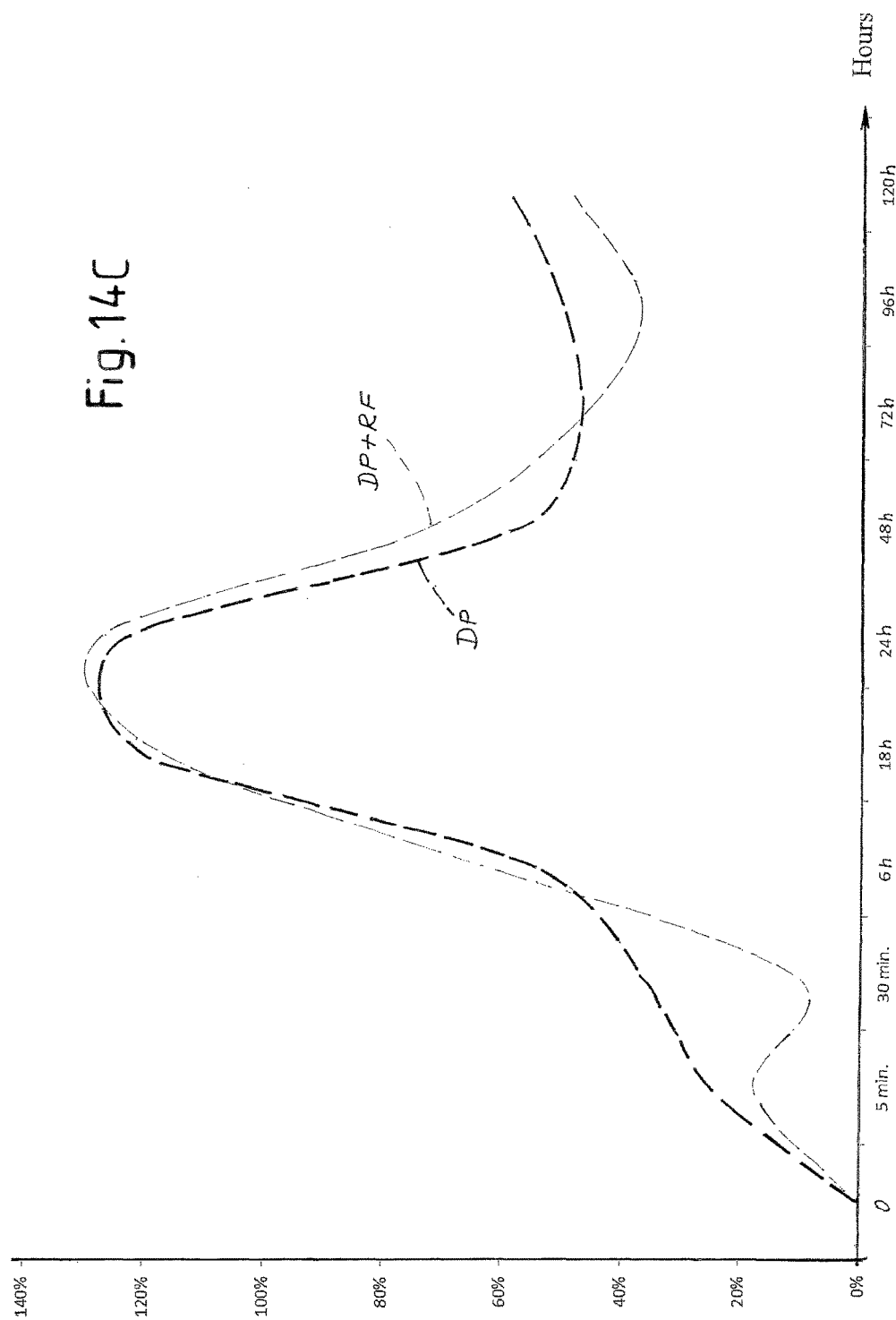

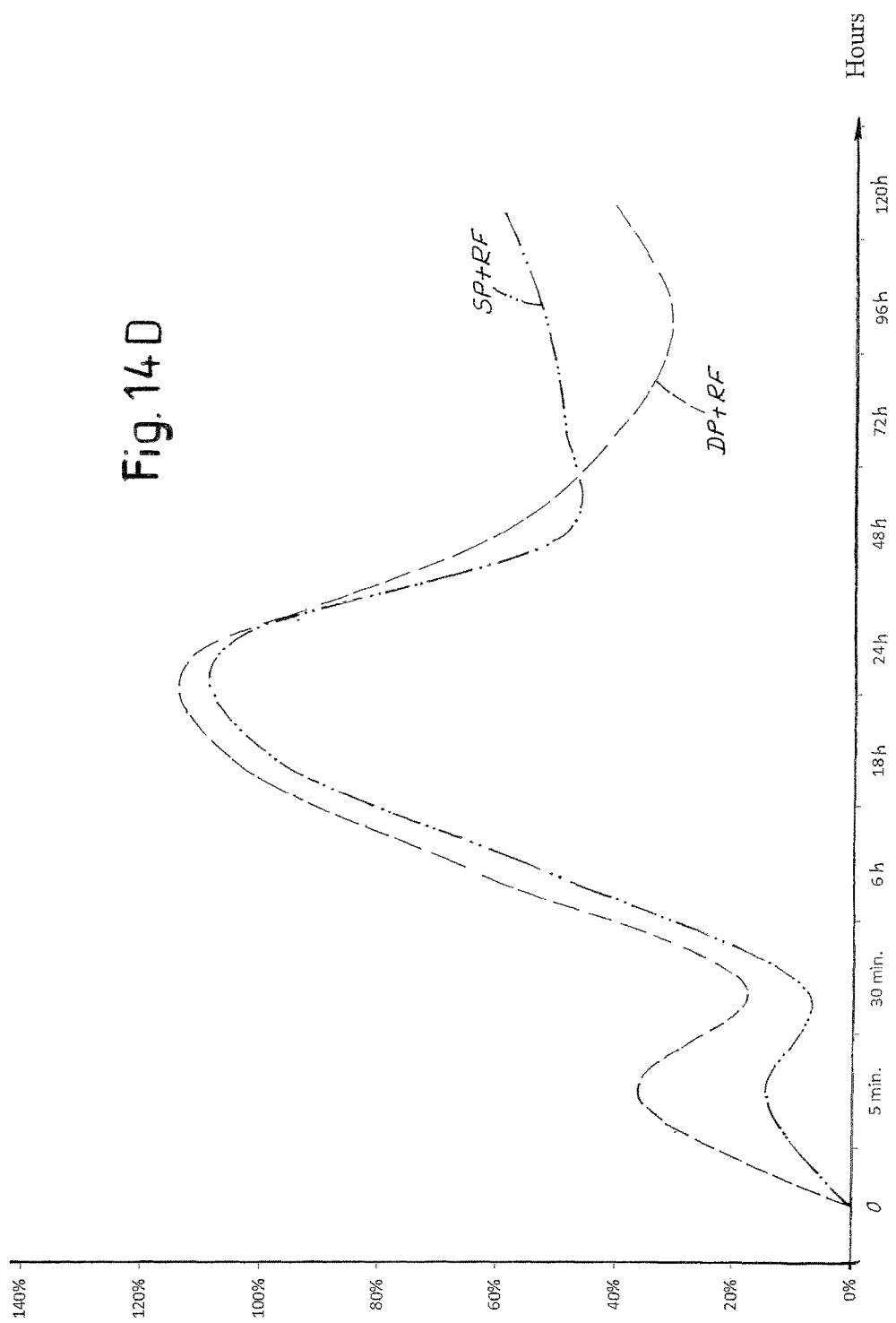

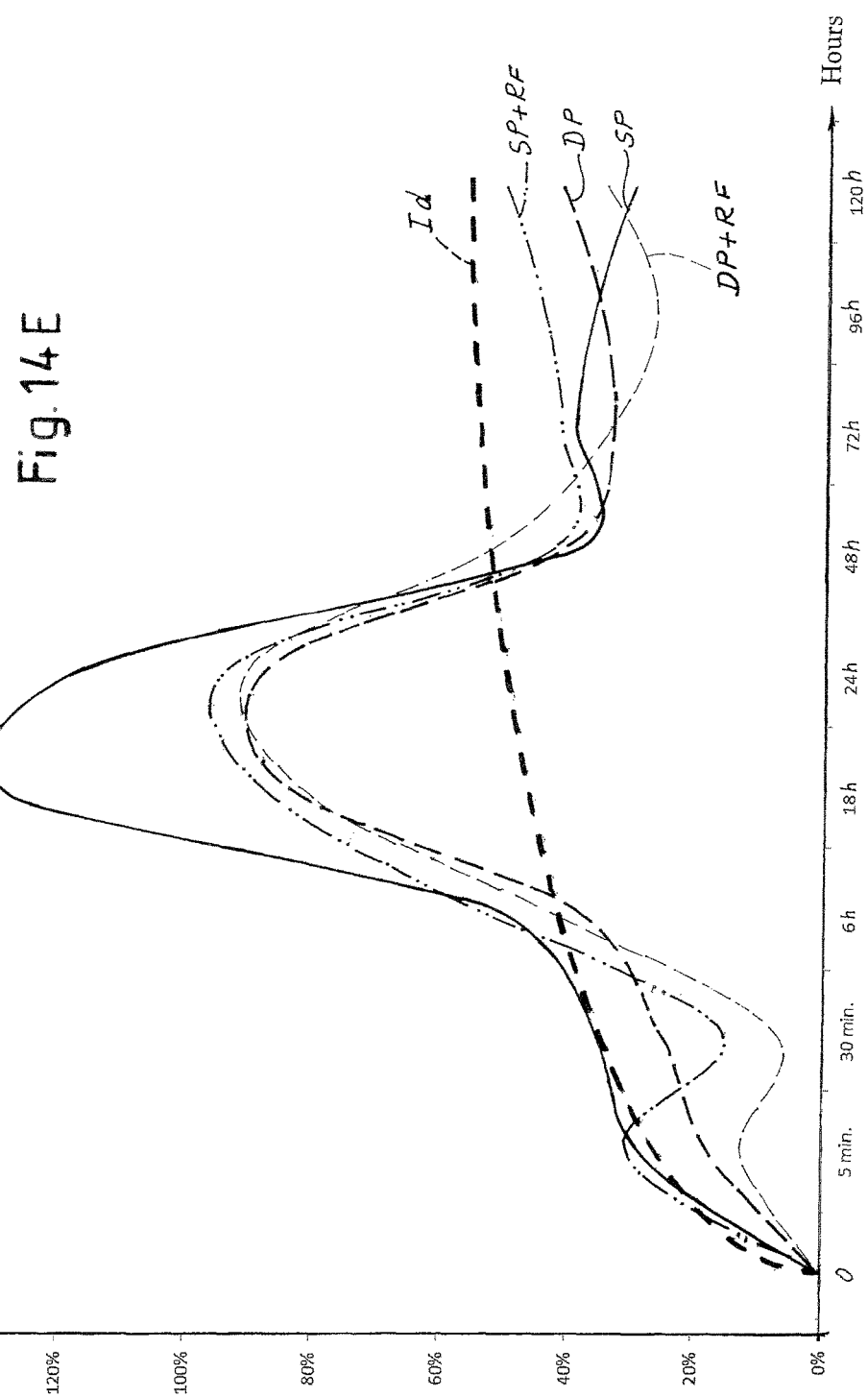

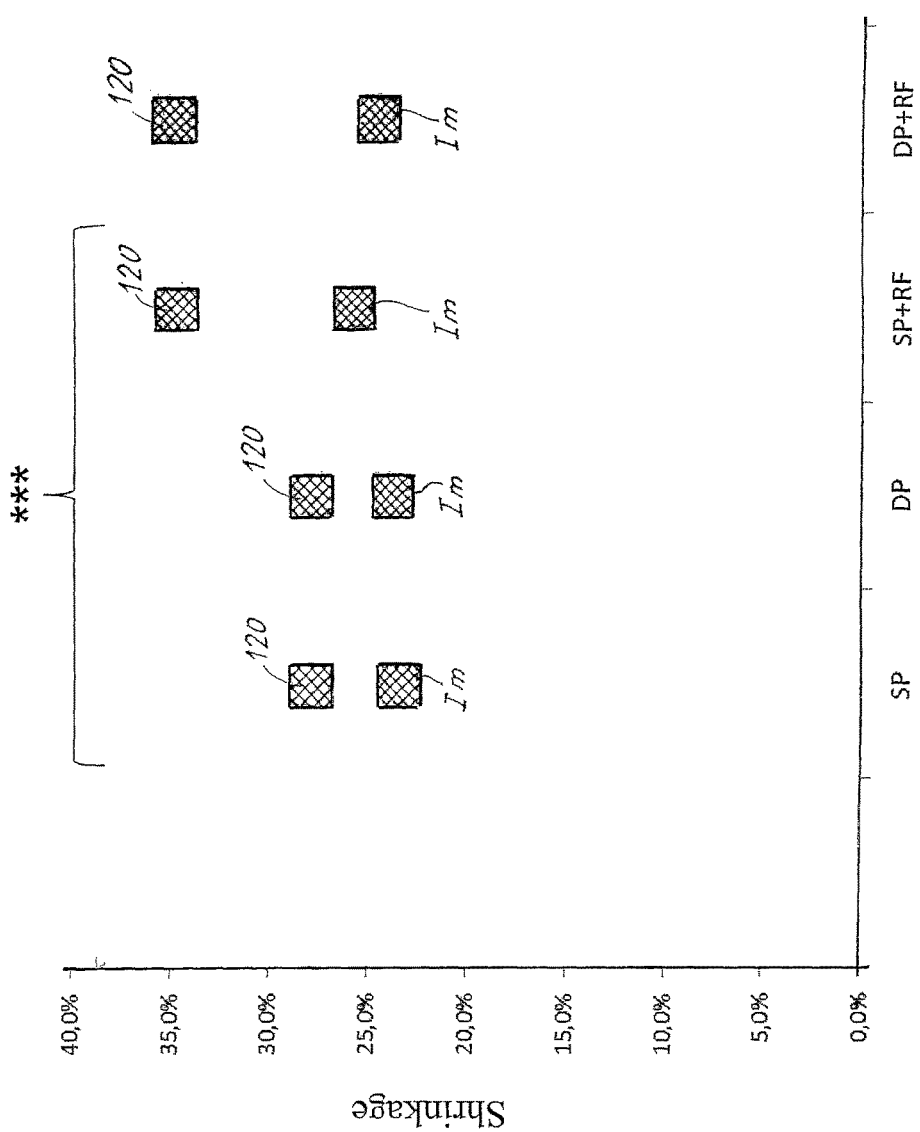

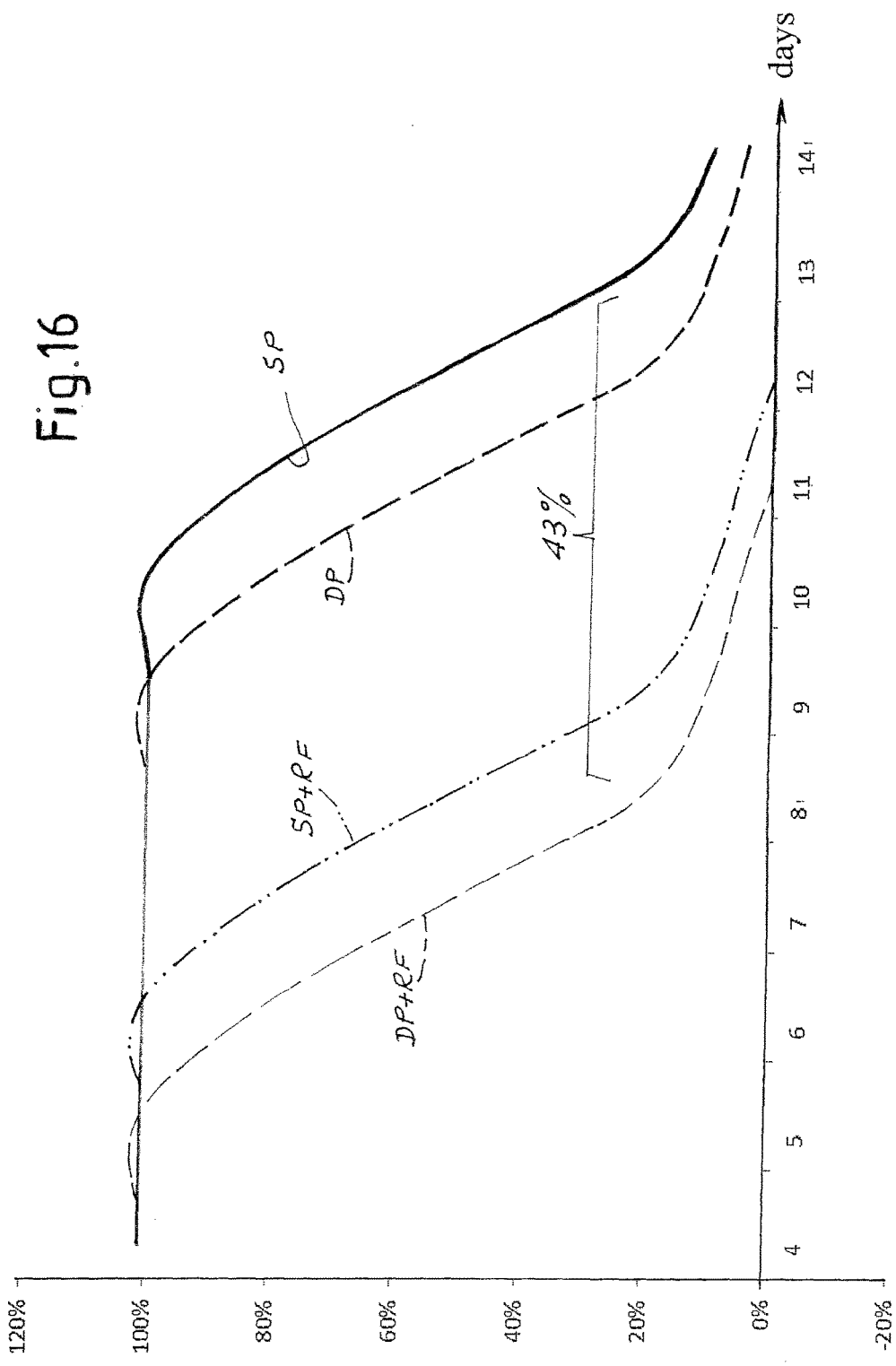

DEVICE AND METHOD FOR SKIN LASER TREATMENT

TECHNICAL FIELD

The present invention relates to a device and a method for skin treatment. More in particular, the present invention relates to a device and a method for treatment using an apparatus comprising a laser beam of suitable wavelength, optionally combined with an RF current, to obtain given effects on the epidermis, such as wrinkles reduction and a general rejuvenating effect.

BACKGROUND OF THE INVENTION

Medical and cosmetic treatments to improve the appearance of the person, to solve problems related to skin blemishes and also to deal with and solve situations of true psychological distress deriving from the subject's inability to accept his or her appearance, are becoming increasingly widely used.

Among the various procedures, methods and machines used, a vast number of cases are dedicated to treatments aimed at reducing the effects of aging and, therefore, in particular, at eliminating or reducing the formation of wrinkles on the face and on other parts of the body, such as the neck and the upper part of the chest. In recent times, techniques have been developed for treating the epidermis using laser. In many applications, the portion of epidermis to be treated is irradiated in a practically uniform manner by a laser beam, which performs a surface ablation process, with consequent elimination of the upper layers of the epidermis.

The use of the laser in treatment of the epidermis, especially of the face, to reduce wrinkles and other skin blemishes is described, among others, in the following works: Chernoff G, Slatkine M, Zair AND, Mead D., "Silk-Touch: a new technology for skin resurfacing in aesthetic surgery", in J Clin Laser Med Surg. 1995 April; 13(2):97-100; Waldorf H A, Kauvar A N, Geronemus R G; "Skin resurfacing of fine to deep rhytides using a char-free carbon dioxide laser in 47 patients.", in Dermatol Surg. 1995 November; 21(11):940-6; David L M, Same A J, Unger W P., "Rapid laser scanning for facial resurfacing.", in Dermatol Surg. 1995 December; 21(12):1031-3; Lask G, Keller G, Lowe N, Gormley D., "Laser skin resurfacing with the SilkTouch flashscanner for facial rhytides.", in Dermatol Surg. 1995 December; 21(12):1021-4; Apfelberg D B., "Ultrapulse carbon dioxide laser with CPG scanner for full-face resurfacing for rhytids, photoaging, and acne scars", in Plast Reconstr Surg. 1997 June; 99(7):1817-25; Apfelberg D B, Smoller B. "UltraPulse carbon dioxide laser with CPG scanner for deepithelialization: clinical and histologic study", in Plast Reconstr Surg. 1997 June; 99(7): 2089-94; Raulin C, Drommer R B, Schönermark M P, Werner S., "Facial wrinkles—ultrapulsed CO2 laser: alternative or supplement to surgical face lift?", in Laryngorhinootologie. 1997 June; 76(6):351-7; Trelles M A, Rigau J, Mellor T K, García L., "A clinical and histological comparison of flashscanning versus pulsed technology in carbon dioxide laser facial skin resurfacing", in Dermatol Surg. 1998 January; 24(1):43-9; Weinstein C., "Computerized scanning erbium:YAG laser for skin resurfacing", in Dermatol Surg. 1998 January; 24(1):83-9; Bernstein L J, Kauvar A N, Grossman M C, Geronemus R G., "Scar resurfacing with high-energy, short-pulsed and flashscanning carbon dioxide lasers", in Dermatol Surg. 1998 January; 24(1):101-7; Vaïsse V, Clerici T, Fusade T., "Bowen disease treated with scanned pulsed high energy CO2 laser. Follow-up of 6 cases", in Ann. Dermatol. Venereol. 2001 November; 128 (11):1220-4.

In recent times, methods have been developed in which treatment of the epidermis is discontinuous (known as "fractional" technology), i.e. on a given region to be treated the laser is focused in discrete areas, separated from one another by areas that are not irradiated by the laser beam. The zones irradiated by the laser beam are subjected to ablation in substantially cylindrical volumes, spaced apart from one another by large volumes in which no treatment is carried out. Methods of this type are described in Toshio Ohshiro et al, "*Laser Dermatology—State of the Art*", proceedings of the 7th Congress International Society for Laser Surgery and Medicine in Connection with Laser 87 Optoelectronics, ed. Springer-Verlag, 1988, page 513 ff. The same methods are described in U.S. Pat. No. 6,997,923.

In this way, attempts are made to combine the requirement of tissue ablation, which causes localized damage of the tissue and erythema due to the noteworthy heating produced by the laser, with the need for a minimally invasive procedure. It was deemed that by acting on limited tissue portions spaced apart from one another by wide zones not affected in by the laser beam, it would be possible to obtain treatment effects (such as reduction or elimination of wrinkles) equivalent to those obtained with a full volume or full surface area treatment of conventional type, but with fewer secondary effects of damage to the epidermis, a decrease in the formation of erythema and in general a reduction in post-treatment recovery times.

In the literature, procedures of this type are described, among others, in the following works: Fitzpatrick R E, Rostan E F, Marchell N., "Collagen tightening induced by carbon dioxide laser versus erbium: YAG laser", in Lasers Surg. Med. 2000; 27(5):395-403; Hasegawa T, Matsukura T, Mizuno Y, Suga Y, Ogawa H, Ikeda S., "Clinical trial of a laser device called fractional photothermolysis system for acne scars", in Dermatol. 2006 September; 33(9):623-7; Rahman Z, Alam M, Dover J S., "Fractional Laser treatment for pigmentation and texture improvement", in Skin Therapy Lett. 2006 November; 11(9):7-11; Laubach H, Chan H H, Rius F, Anderson R R, Manstein D., "Effects of skin temperature on lesion size in fractional photothermolysis", in Lasers Surg Med. 2007 January; 39(1):14-8; Collawn S S., "Fraxel skin resurfacing", in Ann Plast Surg. 2007 March; 58(3):237-40; Hantash B M, Bedi V P, Chan K F, Zachary C B., "Ex vivo histological characterization of a novel ablative fractional resurfacing device", in Lasers Surg Med. 2007 February; 39(2):87-95; Hantash B M, Bedi V P, Kapadia B, Rahman Z, Jiang K, Tanner H, Chan K F., "In vivo histological evaluation of a novel ablative fractional resurfacing device", in Lasers Surg Med. 2007 February; 39(2):96-107.

The efficacy of these methods is debatable. In particular, acting on volumes that are too close together it is not possible to obtain particular improvements in terms of reduction of recovery times, while treating volumes that are spaced too far from one another by untreated zones involves the risk of insufficient results and consequent need for a second treatment.

The use of radiofrequency current is also known in aesthetic treatments. See for example Goldberg D J, Fazeli A, Berlin A L. "Clinical, laboratory, and MRI analysis of cellulite treatment with a unipolar radiofrequency device", in Dermatol Surg. 2008 February; 34(2):204-9; or Montesi G, Calvieri S, Balzani A, Gold M H., "Bipolar radiofrequency in the treatment of dermatologic imperfections:

clinicopathological and immunohistochemical aspects", in J. Drugs Dermatol. 2007 February; 6(2):212-5.

WO-A-02/26147 and U.S. Pat. No. 6,702,808 describe a system for treatment of the epidermis in which a radiofrequency current is combined with optical energy. The treatment described in this publication provides for the simultaneous application of optical and radiofrequency radiation. The characteristics of the optical radiation used are not described in detail, although it is indicated that their wavelength ($\lambda$) must be no greater than 1200 nm.

SUMMARY OF THE INVENTION

The object of the invention is to provide a technology that is the result of a combination of different technologies according to precise relations of proportionality both of time and space to obtain a synergistic effect, i.e. a treatment efficacy that exceeds the sum of the results obtainable with the different technologies separately.

Typical applications concern aesthetic skin treatments, in particular with the object of obtaining a reduction of wrinkles, tightening and overall rejuvenation of the tissue. Therefore, the invention also relates to cosmetic treatment methods of the skin and of the underlying tissue through application of optical laser radiation.

In particular, compared to conventional resurfacing the fractional technology used to date has the advantage of having a much less complicated postoperative course, at the same time ensuring excellent recovery of skin texture, reduction of porosity, increased brightness and elasticity. The limit of these technologies consist in their poor efficacy on loose skins, for which it is not possible to stimulate to any significant extent the deep structures of the dermis, without using overly aggressive parameters, which go against the minimally invasive approach inherent to fractional technology.

From the international literature and the patent bibliography it can be seen how the formation of plasma with $CO_2$ laser is dependent on the time shape of the pulse. In order to transfer an appropriate heat wave to the reticular dermis while preventing the onset of undesirable side effects, the invention is based on a new time distribution of the energy in the pulses that takes account of the physical laws for the formation of plasma and therefore of plasma mediated ablation.

According to one aspect, to solve problems of the prior art, either completely or in part, the invention provides a system for the treatment of a region of the epidermis comprising:
  at least one laser energy source;
  a time control device to generate a laser beam;
  a laser energy focusing system arranged and designed to direct a laser beam on said region of the epidermis;
wherein said control device generates a laser beam comprising a plurality of composite pulses, emitted at a base frequency, each composite pulse comprising a sequence of sub-pulses at a higher frequency than said base frequency.

According to a different aspect, the invention relates to a cosmetic method for treating a portion of epidermis of a patient, comprising the step of emitting a laser beam comprising one or more composite pulses, emitted at a base frequency, each composite pulse comprising a sequence of sub-pulses at a higher frequency than said base frequency.

The composite pulse can advantageously comprise a pre-pulse at a higher fluence and one or more subsequent sub-pulses at a lower fluence. The laser pulses can be combined with the application of radiofrequency current.

The term "focusing system" is intended both as a dynamic system, comprising a scanning device, to move the beam to different positions, and as a static system, where an appropriate optic divides, for example, an initial beam into a plurality of adjacent beams arranged according to an appropriate pattern, for example according to a matrix.

In some embodiments of the invention, the laser energy focusing system is arranged and controlled to treat contiguous volumes of the epidermis distributed according to a pattern, wherein each volume treated has a center substantially positioned on the axis of the laser beam used to treat said volume, the axes of the laser beams used to treat said contiguous volumes being distributed according to a presettable matrix of points.

Given a portion of epidermis to be treated, this can be irradiated simultaneously by a plurality of beams, for example obtained with particular optics from a single beam. The various beams are, for example, arranged according to an appropriate pattern, for example a matrix. Preferably, however, a single beam or even more than one beam can be used, to which a scanning movement is imparted according to coordinates (for example Cartesian or polar). In some embodiments, emission of the laser pulse is controlled so that single pulses of laser energy are "fired" in sequentially variable positions along a pre-set pattern, for example according to the points of a matrix.

In other embodiments, the laser beam can be moved from one position to the other without interrupting the energy emission, providing a sufficiently short time for moving from one treatment position to the other. In this way, the effect of the laser during movement from one irradiation point to the other is substantially negligible when compared with the effect of the beam during the dwell phase in a given point or position of the irradiation pattern.

In all cases adjacent beams (irradiated simultaneously, or sequentially with a scanning system) can have overlapping zones, i.e. zones in which the effect of two adjacent beams (or also three or more adjacent beams) are overlapped and summed. Naturally, also as a function of the scanning or multiple beam operation and, in the first case, of the scanning time, space overlapping only or else space and time overlapping of beams must be taken into account.

According to a further aspect, the invention relates to a system for treating a epidermis region, comprising:
  at least one laser energy source to generate a pulsed laser beam;
  a laser energy focusing system arranged and designed to direct a laser beam on said region of the epidermis;
  a radiofrequency current source with at least one electrode for applying the radiofrequency current;
  at least one control device which controls the laser energy source and the radiofrequency current source so as to emit said laser beam and said radiofrequency current in a timely coordinated manner.

In some embodiments the control device is designed to emit the radiofrequency current in a time interval at least partly overlapping a time interval of emission of the pulsed laser beam and/or in a time interval subsequent to a time interval of emission of the pulsed laser beam.

Further advantageous features and embodiments of the invention are described hereunder and are indicated in the appended claims, which form an integral part of the present description. The brief description provided above identifies characteristics of the various embodiments of the present invention so that the following detailed description can be better understood and so that the present contributions to the art may be better appreciated. Naturally, there are other characteristics of the invention which will be described below and will be set forth in the appended claims. With reference to this, before illustrating different embodiments of the invention in detail, it must be understood that the various embodiments of the invention are not limited in their application to the structural details and to the arrangements of components described in the following description or illustrated in the drawings. The invention can be implemented in other embodiments and implemented and put into practice in various ways. Moreover, it must be understood that the phraseology and terminology employed herein are purely for descriptive purposes and must not be considered limiting.

Therefore, those skilled in the art will understand that the concept on which the description is based can be readily used as a basis to design other structures, other methods and/or other systems to implement the various objects of the present invention. Consequently, it is important that the claims are considered as inclusive of those equivalent structures which do not depart from the spirit and from the scope of the present invention.

BRIEF DESCRIPTION OF THE DRAWINGS

The invention will be better understood by following the description and accompanying drawing, which shows practical non-limiting embodiments of the invention. More in particular:

FIG. 1 shows a diagram of a device embodying the invention;

FIG. 2 shows a detail of the handpiece of the device of FIG. 1;

FIG. 6 schematically shows an improved handpiece for combined laser and radiofrequency treatment;

FIGS. 6A, 6B, 6C and 6D schematically show an improved embodiment of an electrode for applying radiofrequency current;

FIG. 7 shows the use of the handpiece of FIG. 6;

FIGS. 8 and 9 show the shape of the laser pulse in two different embodiments;

FIGS. 11A, 11B, 12A, 12B, 12C show a schematic representation of the effect of ablation and of thermal shock in the tissue treated with different types of laser pulses according to the invention;

FIG. 13 shows a diagram of the conductivity of the tissue as a function of the frequency of a radiofrequency electrical current;

FIGS. 14A-14E show diagrams of the trend over time of hemoglobin in a tissue treated with laser pulses according to the invention with and without application of radiofrequency electrical current;

FIG. 15 shows a diagram illustrating the shrinkage effect provoked by the different types of treatment;

FIG. 16 shows a diagram illustrating the speed of disappearance of skin reddening caused by the treatment in various treatment conditions;

DETAILED DESCRIPTION OF EMBODIMENTS OF THE INVENTION

Figure 3:
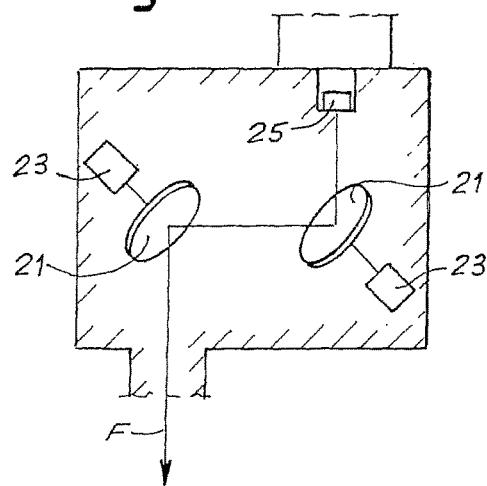
FIG. 3 shows a diagram of a laser-beam scanning system.

Structure of the Handpiece and of the Optics

The following detailed description of exemplary embodiments refers to the accompanying drawings. The same reference numbers in different drawings identify identical or similar elements. Moreover, the drawings are not necessarily in scale. Further, the following detailed description does not limit the invention. Rather, the scope of the invention is defined by the appended claims.

Reference in the whole of the description to "an embodiment" or "the embodiment" or "some embodiments" means that a particular feature, structure or element described in relation to an embodiment is included in at least one embodiment of the subject described. Therefore, the phrase "in an embodiment" or "in the embodiment" or "in some embodiments" in various points throughout the description does not necessarily refer to the same embodiment or embodiments. Moreover, the particular features, structures or elements can be combined in any suitable manner in one or more embodiments.

FIGS. 1 and 2 show a device in which the invention can be incorporated. In general, the device 1 comprises a base 3, wherein at least one laser source 5 is housed. The laser source 5 can be a continuous laser, but preferably a pulsed laser is used. The block indicated generically with 5 is intended also as including a system to control the emission in time of the laser radiation, i.e. the pulse generation system.

According to some embodiments, the laser source can have an emitting wavelength comprised between 532 and 13,000 nm and more in particular a wavelength of 10600 nm, corresponding to $CO_2$ laser emission. In fact, the laser source is preferably a $CO_2$ laser.

In some modes of use, the laser can be controlled so as to provide a pulse for each position or point of a treatment pattern. However, in other modes of use more than one laser pulse can be "fired" for each operating position, i.e. at each point treated. For example, from two to five pulses can be provided for each position of the laser. Preferably, the laser is controlled so as to be able to emit one or more pulses for each position or point of the pattern on the portion of epidermis to be treated, depending on the settings chosen by the operator. Movement of the laser beam can be obtained through a system of scanning mirrors described in greater detail below. Preferably, the laser emission is interrupted when moving from one treatment position to the other, i.e. from one point to the other of a treatment pattern.

Advantageously, in some embodiments the laser beam has a Gaussian power distribution, with a maximum power density at the center and decreasing toward the periphery of the cross section of the beam. To obtain the Gaussian shape of the beam, in some embodiments the laser cavity is produced so as to isolate the fundamental propagation mode and the focusing optics must be designed to contribute to maintaining the Gaussian shape of the energy distribution when moving from the axis outwardly. An appropriate choice of cavity diameter and an appropriate radius of the mirrors of the laser source are able to provide generation of the TEM00 oscillation mode that provides a Gaussian beam profile.

The laser beam can be conveyed through a waveguide 7 toward a handpiece 9. The guide can be designed in various ways, also depending upon the frequency and the emission power of the laser. In the example illustrated the waveguide is simply made of hollow tubular elements, joined to one another and inside which mirrors for deflecting the laser beam are arranged to deviate the beam along the axis of the various tubular portions of the guide.

Figure 4:
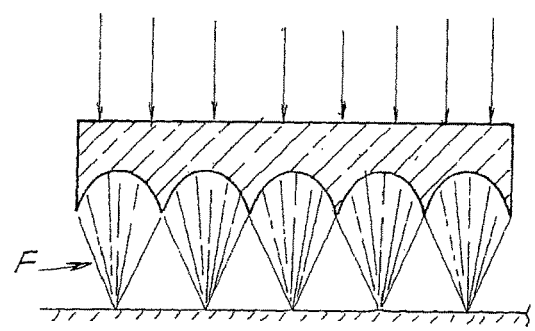
FIG. 4 shows a diagram of a system for dividing a main laser beam in a plurality of adjacent or contiguous laser beams.

Inside the handpiece 9 there are arranged focusing systems and/or scanning of the laser beam, some of which are represented schematically in FIGS. 3 and 4. Preferably in the handpiece 9 there is contained a scanning system (FIG. 3) comprising for example two scanning mirrors 21 with related actuators 23 controlled electronically by a control unit, not shown. The scanning mirrors control the movement of the laser beam F output from the handpiece 13, so that it follows a given path, according to criteria better defined below. Therefore, in this case a single laser beam F is outputted from the handpiece and directed toward the surface of the epidermis to be treated, from which the handpiece can be held at a constant distance, for example by means of a spacer 11. On the handpiece 13 push buttons, knobs or other adjustment and interface members can be arranged, schematically indicated with 15, through which the operator can modify the shape of the beam and/or the dimension and the area of the scanning surface, the movement of the beam and the like.

Through the handpiece 13 and the scanning system contained therein it is possible to control movement of the beam F according to a defined and stored pattern, optionally modifiable by the user.

In a suitable position along the path of the laser beam a focusing optic is arranged. In the diagram of FIG. 3 said optic is indicated with 25 and is placed in the handpiece, but it must be understood that this is not strictly necessary and that other positions are possible. The optic 25 also has the function of imposing on the beam a given energy density distribution as a function of the radius, as will be clarified below.

In other embodiments, inside the handpiece 13 there are arranged focusing systems which divide the laser beam into a plurality of beams adjacent to one another and which impart to each of the adjacent beams an energy density profile as a function of the radius according to the criteria described below.

In some embodiments the lens placed in the handpiece in combination with the shape of the beam generated by the source give rise to a Gaussian energy density distribution profile. The shape of the beam generated depends on the purity of the propagation mode inside the laser cavity which consequently determines the energy distribution transverse to the axis of propagation in the free space at the output of the laser source.

In some embodiments the beams with which the portion of epidermis to be treated is irradiated can be adjacent beams generated with an optical system of the type represented in FIG. 4, or can simply be represented by positions assumed in time sequence by a same laser beam which is moved by a scanning system as represented in FIG. 3. In this latter case, the laser beam is preferably switched on, i.e. activated sequentially in each position desired according to a radiation pattern, while during movement between one point and the other the laser is preferably switched off.

Figure 5:
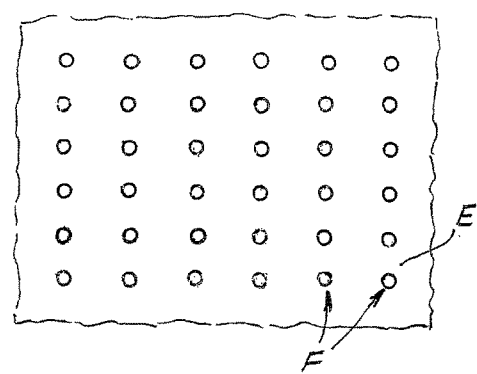
FIG. 5 shows a matrix according to which the laser treatment points of a portion of epidermis can be arranged.

Whatever the system for generating the adjacent laser beams, the epidermis can be irradiated, for example, following a pattern with a matrix of points, as indicated schematically in FIG. 5. The letter E generically indicates a treated portion of epidermis and the letter F the points of intersection between the axis of the laser beam and the surface of epidermis being treated. It must be observed that in this case the treatment pattern is formed by a plurality of points arranged according to a matrix or grid with rectangular mesh, the vertices of which form the points in which the center of the laser beam is positioned. One or more laser pulses can be emitted in each position represented by a point F.

It must be understood that the pattern of FIG. 5 is provided purely by way of example and that different patterns can be used, for example according to a matrix with rhomboidal mesh, or also a pattern in which the points F are arranged according to curved lines, according to a spiral or in any other way. Currently, a pattern according to a matrix with quadrangular, i.e. rectangular or rhomboidal, mesh is preferred.

The shape of the laser pulses used and the values of the emission parameters, and the results obtained with various shapes of laser radiation will be discussed below.

According to improved embodiments of the invention, the laser treatment is combined with a treatment through applying radiofrequency. FIGS. 6 and 7 illustrate this embodiment. FIG. 6 shows a handpiece 109, which contains the same components as the handpiece 9, in addition to a radiofrequency generator, indicated schematically with 110. The radiofrequency generator is connected to a pair of electrodes 113. In some embodiments the electrodes 113 are shaped to form a spacer between the handpiece 109 and the surface to be treated. The distance is determined on the basis of the optical characteristics of the laser, whose radiation is conveyed to the handpiece 109 through a light guide 115, as in the embodiment described previously. Interface means between the appliance and the user are provided on the handpiece 109, such as one or more push buttons or the like, generically indicated with 117.

Using the electrodes as spacers, an instrument that is particularly compact, inexpensive and easy to use is obtained.

With a handpiece of this type it is possible to synergistically combine the effects of laser and of radiofrequency on the treated tissue. When the electrodes 113 are resting on the skin to be treated, for example on the patient's face, as shown in FIG. 7, the radiofrequency field generated by the electrodes propagates into the tissues and generates induced currents, which heat the treated tissue.

FIGS. 6A, 6B, 6C and 6D schematically show an improved embodiment of an electrode for applying radiofrequency current which prevents or reduces the risk of generating electrical arcs between the electrode and the epidermis of the subject treated when the electrode is moved away from the skin. In this embodiment a device is provided for switching off the electrical power circuit of the RF current, which opens the circuit and cuts off the electrical power inside a protected zone, preventing electrical discharges from generating on the skin. In particular, the electrode 113 can have ends 113A (FIG. 6D) seated in respective cases 114. The ends 113A form first contacts cooperating with second contacts 118 housed in the respective cases 114. The contacts 113A, 118 form a pair of switches which are closed as a result of compression of respective springs 120, advantageously housed in the cases 114, when the electrode 113 is pressed against the skin. Compression of the springs 120 causes the ends 113A of the electrode 113 to contact the contacts 118, closing the electrical circuit. When the operator moves the handpiece 109 on which the electrodes 113 are placed away from the patient's skin, the springs 120 extend, causing the contacts 113A, 118 to move away from each other and consequent opening of the electrical circuit. Any arcs o discharges remain confined inside the cases 114.

It must be understood that an electrode 113 with one movable end 113A and the other end permanently connected to the electrical circuit could also be used. The elastic effect can also be obtained by means of properties of the material with which the electrode 113 is made, without the need to use an auxiliary spring. For example, the electrode 113 can be made in the form of flat spring, with an advantageously arcuate shape. One end of electrode is fixed and the other forms a movable contact which approaches a fixed contact, enclosed in a protected zone, when the handpiece is pressed onto the skin, closing the electrical circuit.

Alternatively to the use of movable contacts, or in combination therewith, a sponge 116, either made of conducting material or preferably made conductive by impregnating it with a conductive liquid, such as a saline solution, can be associated with the electrode 113. The sponge 116 can be shaped appropriately, for example with a groove, to be reversibly fixed to the electrode 113. The sponge 116 can advantageously be disposable, for reasons of hygiene.

Laser radiation and radiofrequency can be combined or overlapped in time in various ways, according to criteria that will be clear from the description set forth below.

The results of the combined application of optical radiation and RF current and some possible explanations of the particular efficacy obtainable with this method will be discussed below.

Time Shape of the Laser Beam

It has been discovered, and is an important element of the present invention, that particular shapes of the pulse of the laser radiation, i.e. particular trends over time of the pulsed laser emission, enable much greater biological effects to be obtained on tissue, compared to prior art systems. It has also been discovered that in some cases the laser pulses shaped according to the invention have a synergistic effect in combination with a radiofrequency current. As will be illustrated below, the shapes of the pulses according to the invention enable more efficient treatments and faster healing, especially in skin-tissue rejuvenating and firming treatments.

FIG. 8 shows a first time shape of a series of laser pulses according to the invention, i.e. the trend over time of the laser light emission. In this figure, the abscissa indicates the time and the ordinate indicates the emitted power.

Hereinafter the laser pulse having the shape of FIG. 8 will be indicated as "pulse S". Said pulse is in fact a composite pulse, where composite pulse is intended as a pulse that is in turn constituted by the combination of sub-pulses, or hypo-energy pulses, as will be described in detail below.

FIG. 8 shows a sequence of pulses SP with the period T. A period T has an on interval τ-on and an off interval τ-off. The sum of the time intervals τ-on and τ-off is equal to the period T of the pulse. The relation τ-on/T is defined as the duty cycle of the composite pulse. The inverse 1/T of the period T of the composite pulse is defined as the frequency of the composite pulse. According to some embodiments, the frequency of the composite pulse, hereinafter also defined as base frequency, is comprised between 1 and 1000 Hz, for example between 1 and 500 Hz. The duty cycle of the composite pulse can be comprised between 1% and 90% and preferably between 2% and 50% and even more preferably between 2% and 40%.

As can be observed in FIG. 8, sub-pulses Si are contained in the interval τ-on of each composite pulse. In the embodiment of FIG. 8 sub-pulses, all of the same duration, are contained in the interval τ-on. In some embodiments the sub-pulses Si have a frequency comprised between 1 kHz and 200 kHz. In preferred embodiments the frequency of the sub-pulses is comprised between 1 kHz and 100 kHz and even more preferably between 2 kHz and 50 kHz. In some embodiments the frequency is comprised between 5 and 45 kHz, for example between 8 and 40 kHz.

The duty cycle of the sub-pulses, i.e. the relation between the period of the sub-pulse, indicated with Ts in FIG. 8, and the duration of the on-interval (during which sub-pulses are emitted) is determined as a function of the peak power, of the duration τ-on of the composite pulse and of the energy per pulse that is required to be emitted at each pulse. In some embodiments the on-duration of the single sub-pulse is comprised between 1 and 50 microseconds and preferably between 2 and 40 microseconds. In some embodiments, the duration of the on-period is between 3 and 25 microseconds. The duty cycle can be comprised between 1 and 90% and preferably between 1 and 50% and even more preferably between 2 and 25%. Typically, the duty cycle is comprised between 3 and 24%.

La peak power, indicated in FIG. 8, can be comprised between 10 and 200 W, preferably between 40 and 190 W.

In some embodiments the energy per pulse of the composite pulses is comprised between 0.2 and 200 mJ, for example between 0.4 and 150 mJ and preferably between 0.4 and 130 mJ.

The energy of the single sub-pulse Si can be comprised between 0.2 and 10 mJ and preferably between 0.4 and 8 mJ.

The spot area, i.e. the area of the section of the laser beam on the surface onto which the beam is projected, is advantageously comprised between 0.0001 and 0.0003 $cm^2$ and preferably between 0.00015 and 0.0002 $cm^2$. The fluence, i.e. the energy per unit of surface area, is obtained as the ratio between the powers and the spot areas indicated above. According to some embodiments the diameter of the spot is comprised between 50 and 500 micrometers, preferably between 80 and 400 micrometers, even more preferably between 100 and 200 micrometers, for example around 150 micrometers.

The average power can be comprised between 2 and 100 W, for example between 4 and 80 W, preferably between 4 and 50 W.

In some embodiments of the invention the number of pulses Si for each train or composite pulse can be comprised between 1 and 100 and preferably greater than 1 and less than or equal to 80.

The following tables 1 and 2 each indicate two series of values for the main parameters of the pulse. It must be understood that each parameter may vary in the interval defined by the two values of the corresponding line.

TABLE 1

| | | |
|---|---|---|
| Repetition frequency (Hz) | 10,000 | 10,000 |
| Duration of the sub-pulse (µs) | 100 | 100 |
| On time of the sub-pulse (µs) | 4 | 24 |
| Off time of the sub-pulse (µs) | 96 | 76 |
| Duty Cycle (%) of the sub-pulse | 4% | 24% |
| Peak power of the sub-pulse (W) | 12 | 180 |
| Energy of the sub-pulse (mJ) | 0.4 | 6.0 |
| Total energy of the train of pulses (mJ) | 0.4 | 120.0 |
| Number of pulses per train (i.e. per composite pulse) | 1 | 20 |
| Spot diameter (µm) | 150 | 150 |

TABLE 1-continued

| | | |
|---|---|---|
| Spot area (cm²) | 0.0001767146 | 0.0001767146 |
| Fluence of the single sub-pulse (J/cm²) | 2.26 | 33.95 |
| Fluence of the composite pulse (J/cm²) | 2.26354 | 679.06109 |
| Average power (W) | 4 | 60 |
| Dwell time (μs) | 100 | 2000 |

TABLE 2

| | | |
|---|---|---|
| Repetition frequency (Hz) | 40,000 | 40,000 |
| Duration of the sub-pulse (μs) | 25 | 25 |
| On time of the sub-pulse (μs) | 1 | 6 |
| Off time of the sub-pulse (μs) | 24 | 19 |
| Duty Cycle (%) of the sub-pulse | 4% | 24% |
| Peak power of the sub-pulse (W) | 6 | 90 |
| Energy of the sub-pulse (mJ) | 0.1 | 1.5 |
| Total energy of the train of pulses (mJ) | 0.4 | 120.0 |
| Number of pulses per train (i.e. per composite pulse) | 4 | 80 |
| Spot diameter (μm) | 150 | 150 |
| Spot area (cm²) | 0.0001767146 | 0.0001767146 |
| Fluence of the single sub-pulse (J/cm²) | 0.57 | 8.49 |
| Fluence of the composite pulse (J/cm²) | 2.26354 | 679.06109 |
| Average power (W) | 4 | 60 |
| Dwell time (μs) | 100 | 2000 |

Table 3 below gives a possible combination of parameters for an exemplary embodiment of a pulse according to the invention.

TABLE 3

| | |
|---|---|
| Repetition frequency (Hz) | 40,000 |
| Duration of the sub-pulse (μs) | 25 |
| On time of the sub-pulse (μs) | 3 |
| Off time of the sub-pulse (μs) | 22 |
| Duty Cycle (%) of the sub-pulse | 12% |
| Peak power of the sub-pulse (W) | 45 |
| Energy of the sub-pulse (mJ) | 0.75 |
| Total energy of the train of pulses (mJ) | 30.0 |
| Number of pulses per train (i.e. per composite pulse) | 40 |
| Spot diameter (μm) | 150 |
| Spot area (cm²) | 0.0001767146 |
| Fluence of the single sub-pulse (J/cm²) | 4.24 |
| Fluence of the composite pulse (J/cm²) | 169.76527 |
| Average power (W) | 30 |
| Dwell time (μs) | 1000 |

FIG. 9 schematically shows the trend over time of the laser emission in an improved embodiment of the invention. Once again, the time is indicated on the abscissa and the power emitted is indicated on the ordinate. As can be seen in the diagram of FIG. 9, in this case each laser pulse is still a composite pulse, in the sense that emission is non-continuous in the emission time interval τ-on, but rather characterized by sub-pulses. Hereinafter, the composite pulse of FIG. 9 is named D pulse and is indicated with DP. FIG. 9 shows a sequence of pulses DP with the period T. A period T has an on-interval τ-on and an off-interval τ-off. The sum of the time intervals τ-on and τ-off is equal to the period T of the pulse DP. The relation τ-on/T is defined as the duty cycle of the composite pulse DP. The inverse 1/T of the period T of the composite pulse DP is defined as the frequency of the composite pulse DP.

According to some embodiments the frequency of the composite pulse DP, hereinafter also defined as base frequency, is comprised between 1 and 1000 Hz, for example between 1 and 500 Hz. The duty cycle of the composite pulse DP can be comprised between 1% and 90% and preferably between 2% and 50% and even more preferably between 2% and 40%.

As can be observed in FIG. 9, the interval τ-on of each composite pulse DP contains: a sub-pulse of greater duration and a train of sub-pulses of lesser duration, preferably equal for each of said shorter sub-pulses. Hereinafter the sub-pulse of greater duration will be indicated as pre-pulse (Pi) or hyper-energy pulse and the subsequent sub-pulses of lesser duration will be indicated as sub-pulses or hypo-energy pulses Si. The portion of the on interval τ-on of the composite pulse DP that follows the pre-pulse Pi is hereinafter also called "tail". Therefore, each composite pulse DP is in turn constituted by a pre-pulse Pi, by a train of sub-pulses Si and by an off interval τ-off. According to one aspect, hyper-energy pulse is intended as a pulse with an energy per unit of surface area such as to generate plasma to remove the epidermis but such as not to interact with the middle layers of the dermis. Hypo-energy is intended as a pulse or sub-pulse with an energy per unit of surface area adapted to generate a "cold" ablation, i.e. without plasma or substantially without plasma, but of sufficient intensity to cause hyperemia and shrinkage of the collagen fibers of the deep levels of the dermis.

In some embodiments, as shown schematically in FIG. 9, the pre-pulse or hyper-energy pulse Pi has a higher peak power than the hypo-energy pulses or sub-pulses Si. For example, the peak power of the latter is from 15 to 70% lower than the peak power of the former.

It would also be possible for the pulses Si and Pi to have the same peak power.

The sum of the time intervals τ-on and τ-off is equal to the period T of the pulse. The relation τ-on/T is defined duty cycle of the composite pulse. The inverse 1/T of the period T of the composite pulse is defined frequency of the composite pulse. According to some embodiments, the frequency of the composite pulse, hereinafter also defined as base frequency, is comprised between 1 and 1000 Hz, for example between 1 and 500 Hz. The duty cycle of the composite pulse can be comprised between 1% and 90% and preferably between 2% and 50% and even more preferably between 2% and 40%.

In some embodiments the sub-pulses Si have a frequency comprised between 1 kHz and 200 kHz. In preferred embodiments, the frequency of the sub-pulses is comprised between 1 kHz and 100 kHz, and even more preferably between 2 kHz and 50 kHz. In some embodiments the frequency is comprised between 5 and 45 kHz, for example between 8 and 40 kHz.

In some embodiments, the pre-pulse Pi has a duration comprised between 10 and 100 microseconds. In improved embodiments of the invention, the pre-pulse has a duration comprised between 20 and 90 microseconds and in particular between 40 and 80 microseconds. Currently, the preferred duration of the pre-pulse is comprised between 50 and 70 microseconds. Optimal results were obtained with a pre-pulse duration of around 60 microseconds.

The duty cycle of the sub-pulses forming the tail of the pulse DP, i.e. the relation between the period of the sub-pulse, indicated with Ts in FIG. 9, and the duration of the on interval of the sub-pulse Si, is determined as a function of the peak power, of the duration τ-on of the composite pulse and of the energy per pulse that is required to be emitted at each pulse.

The duty cycle of the sub-pulses can be comprised between 1% and 90%, preferably between 2 and 50%, more preferably between 2 and 40%.

The peak power of the pre-pulse Pi, indicated as "Peak Power" in FIG. 9, can be comprised between 100 and 500 W, and preferably between 150 and 500 W. In some embodiments the peak power is comprised between 200 and 400 W, for example between 250 and 350 W. It would also be possible to adopt higher peak powers, for example comprised between 250 and 500 W.

The peak power of the sub-pulses or hypo-energy pulses Si can be substantially lower, for example comprised between 20 and 250 W, preferably between 100 and 250 W.

The energy of the pre-pulse can be comprised, for example, between 10 and 40 mJ and preferably between 12 and 25 mJ, even more preferably between 12 and 20 mJ.

In some embodiments the total energy of the train of sub-pulses Si is comprised between 0.4 and 200 mJ, for example between 0.4 and 150 mJ and preferably between 0.4 and 130 mJ.

The energy of the single sub-pulse Si can be comprised between 0.1 and 10 mJ and preferably between 01 and 8 mJ.

The number of hypo-energy sub-pulses Si of each composite pulse is variable for example from 1 to 100 and preferably is greater than 1 and equal to or lower than 80.

The spot area, i.e. the area of the section of the laser beam on the surface on which the beam is projected, is advantageously comprised between 0.0001 and 0.0003 $cm^2$ and preferably between 0.00015 and 0.0002 $cm^2$. According to some embodiments the diameter of the spot is comprised between 50 and 500 micrometers, preferably between 80 and 400 micrometers, even more preferably between 100 and 200 micrometers, for example around 150 micrometers.

The fluence, i.e. the energy per unit of surface area, is obtained as the ratio between the powers and the spot areas indicated above and can be calculated for the pre-pulse or hyper-energy pulse Pi, for each sub-pulse or hypo-energy pulse Si and for the whole train of sub-pulses Si, on the basis of the spot area and of the energy emitted in the interval considered (Pi, single Si or sum of the pulses Si).

The following tables 4 and 5 each indicate two series of values for the main parameters of the pulse. It must be understood that each parameter may vary in the interval defined by the two values of the corresponding line.

TABLE 4

| | | |
|---|---|---|
| Repetition frequency of the sub-pulse Si (Hz) | 10,000 | 10,000 |
| Duration of the sub-pulse (µs) | 100 | 100 |
| On time of the sub-pulse Si (µs) | 4 | 24 |
| Off time of the sub-pulse Si (µs) | 96 | 76 |
| Duty Cycle (%) | 4% | 24% |
| Peak power pulse Si (W) | 100 | 250 |
| Energy of the single sub-pulse Si (mJ) | 0.4 | 6.0 |
| Sum of the energy of the train of pulses Si (mJ) | 0.4 | 120.0 |
| Number of the pulses Si in a composite pulse | 1 | 20 |
| Spot diameter (µm) | 150 | 150 |
| Spot area ($cm^2$) | 0.001767146 | 0.0001767146 |
| Fluence of the single sub-pulse Si (J/$cm^2$) | 2.26 | 33.95 |
| Total fluence of the train of pulses Si (J/$cm^2$) | 2.26 | 679.06 |
| Average power (W) | 4 | 60 |
| Average power pulse | 154 | 67.5 |
| Dwell time (µs) | 100 | 2000 |

TABLE 5

| | | |
|---|---|---|
| Repetition frequency of the sub-pulse Si (Hz) | 40,000 | 40,000 |
| Duration of the sub-pulse (µs) | 25 | 25 |
| On time of the sub-pulse Si (µs) | 1 | 6 |
| Off time of the sub-pulse Si (µs) | 24 | 19 |
| Duty Cycle (%) | 4% | 24% |
| Peak power of the pulse Si (W) | 100 | 250 |
| Energy of the single sub-pulse Si (mJ) | 0.1 | 1.5 |
| Sum of the energy of the train of pulses Si (mJ) | 0.4 | 120.0 |
| Number of the pulses Si in a composite pulse | 4 | 80 |
| Spot diameter (µm) | 150 | 150 |
| Spot area ($cm^2$) | 0.0001767146 | 0.0001767146 |
| Fluence of single sub-pulse Si (J/$cm^2$) | 0.57 | 8.49 |
| Total fluence of the train of pulses Si (J/$cm^2$) | 2.26 | 679.06 |
| Average power (W) | 4 | 60 |
| Average power pulse | 154 | 67.5 |
| Dwell time (µs) | 100 | 2000 |

The following table 6 indicates an example of the values of the aforesaid parameters:

TABLE 6

| | |
|---|---|
| Repetition frequency of the sub-pulse Si (Hz) | 40,000 |
| Duration of the sub-pulse (µs) | 25 |
| On time of the sub-pulse Si (µs) | 3 |
| Off time of the sub-pulse Si (µs) | 22 |
| Duty Cycle (%) | 12% |
| Peak power of the pulse Si (W) | 23 |
| Energy of the single sub-pulse Si (mJ) | 0.375 |
| Sum of the energy of the train of pulses Si (mJ) | 15.0 |
| Number of the pulses Si in a composite pulse | 40 |
| Spot diameter (µm) | 150 |
| Spot Area (cm$^2$) | 0.0001767146 |
| Fluence of the single sub-pulse Si (J/cm$^2$) | 2.12 |
| Total fluence of the train of pulses Si (J/cm$^2$) | 84.88 |
| Average power (W) | 15 |
| Average power pulse | 30 |
| Dwell time (µs) | 1000 |

Table 7 below indicates an example of the values of the significant parameters of the pre-pulse or high energy pulse Pi, usable in combination with the parameters of the pulses Si indicated above:

TABLE 7

| | |
|---|---|
| On time of the sub-pulse Si (µs) | 60 |
| Peak power of the pulse Pi (W) | 300 |
| Energy of the single sub-pulse Pi (mJ) | 15 |
| Spot diameter (µm) | 150 |
| Spot Area (cm$^2$) | 0.0001767146 |
| Fluence of the single sub-pulse Pi (J/cm$^2$) | 84.88 |
| Average power (W) | 250 |

The period T of the composite pulse is given by the sum of the off-period τ-off and of the on-period τ-on, in turn given by the sum of the periods of the pulses Pi and Si. The off-period can be comprised between 0.1 and 5 ms, preferably between 0.5 and 2 ms, and even more preferably between 0.8 and 1.2 ms, for example around 1 ms.

Given a portion of epidermis to be treated, the treatment is carried out by "firing" a train of pulses SP or DP in a plurality of points according to a given pattern on the surface to be treated. The dwell time of the laser in a given point of the pattern determines, together with the repetition frequency of the composite pulse (i.e. the inverse of the period T) the number of composite pulses applied in a given point of the pattern.

The spacing of the points for applying the laser beam can be comprised between 50 micrometers to 1000 micrometers and preferably between 90 and 550 micrometers.

For sufficiently high laser intensities and very short laser pulse durations, the laser-tissue interaction process is mediated by the formation of plasma in proximity of the irradiated surface. Plasma is defined as a macroscopically neutral gaseous phase with a large fraction of ionized particles.

In the optical breakdown process, the photons of the laser pulse generate, in the vicinity of the irradiated surface, a certain number of electrons due to ionization of the molecules that have absorbed them; the intense electrical field of the laser pulse accelerates them greatly and, in a few nanoseconds, the avalanche ionization process that begins can enable very large electron densities, in the order of $10^{20}$ electrons/cm$^3$ (dense plasma) and very high plasma temperatures, in the order of $10^{4\circ}$ C., to be reached. In these conditions, the plasma is optically opaque, with subsequent shielding of the surface of the tissue from the incident beam, due to the high absorption coefficient of the ionized region. Subsequent expansion of the plasma generates a shock wave, which can cause fragmentation and local breakdown of the tissue.

Figure 17:
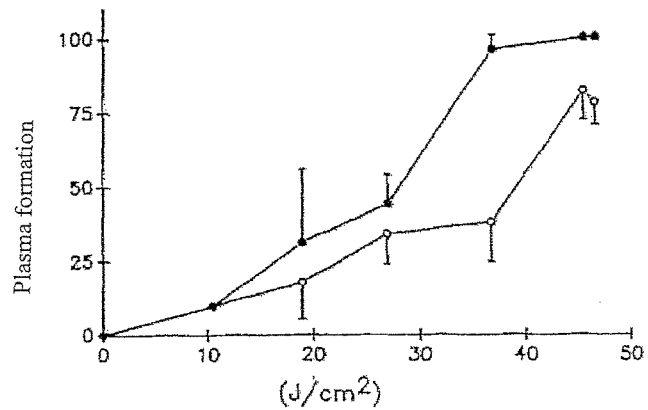
FIG. 17 shows a diagram relating to the formation of plasma as a function of the density of emitted laser energy.

FIG. 17 (taken from Green H A, Domankevitz Y, Nishoka N S. *Pulsed carbon dioxide laser ablation of burned skin: in vitro and in vivo analysis.* Laser Surg Med. 1990; 10(5): 476-84) shows the percentage of plasma formation as a function of the fluence of the $CO_2$ laser. As can be noted, for pulses with energy density comprised between 40-50 J/cm$^2$ the percentage of plasma is very high and the cut is mediated by the plasma itself. Instead, for pulses with low fluence 1-10 J/cm$^2$ the percentage of plasma is more or less negligible and the cut is mediated mainly by laser radiation. In the first case, it is the plasma, generated by the laser itself that produces its biological effects, while in the second case, the laser beam vaporizes the tissue directly. In the first case the temperatures involved are very high, in the order of 10,000° C. with very short dwell times (ns). In the second case, the temperatures involved are in the order of 1,500-2,000° C. but the times are longer (ms). The biological effects obtained in the two cases are very different from each other.

Plasma vaporization is generally preferred to laser vaporization due to its high precision, the very clean residual tissue (as it induces minimum lateral thermal damage) and, above all, due to the almost total absence of charring. In fact, for example in corneal surgery, where the precisions involved must be extremely high, plasma ablation is currently the absolute gold standard. Moreover, when high peak intensities are used, besides being affected by non-negligible thermal effects, laser ablation also suffers from photomechanical effects that limit controllability of the cut by the operator. Instead, in the case of the present invention the photomechanical effects are a positive element as synergistic with the thermal effects for the desired shrinkage of the collagen fibers to be induced to obtain tissue shrinkage.

The main object of some embodiments of the invention is to reach the deep layers of the dermis with the least possible heat front, to induce the least possible lateral thermal damage but, at the same time, which is able to stimulate hyperemia and shrinkage of the collagen fibers. It is known that both phenomena can be activated at medium-low temperatures, i.e. in the interval of 40-70° C. Pulses above the threshold of around 19 J/cm$^2$ are capable of generating plasma and therefore generate, in the ablation cavity, temperatures of over 7,000° C. Around the ablation cavity generated by the plasma (hemispherical shaped), the matter is so destructured that lateral thermal damage is minimum and the tissue is unable to contract. In fact, the collagen fibers are destroyed and the capillaries are dehydrated (for this reason there is no bleeding despite reaching the papillary dermis).

The pulse structured according to the present invention makes use of a hyper-energy laser pulse capable of generating plasma to ablate the portion of epidermis with the least possible lateral thermal damage, thereby reducing to minimum correlated collateral effects, such as re-epithelialization defects due to the presence of carbonaceous residues or to excessive lateral thermal damage. However, on the other hand, excessive increase in heat around the ablation cavity causes widespread collagen destructuring, and in order to find collagen capable of contracting and functional capillaries it is necessary to move away from the ablation cavity by at least a hundred micrometers.

Vice versa, pulses under 19 J/cm$^2$ on average cause a minimum ablation cavity, ensure collagen contraction (shrinkage) even around the ablation cavity and however induce minimum vasodilation of the capillaries as the energy content emitted is decidedly low.

To overcome this limit the stack technology was introduced in the past; this involves multiple repetitions of the aforesaid low energy pulses on each point. This made it possible to reach considerable depths, but to the detriment of tolerability, going against the minimally invasive logic of fractional technology.

Starting from these considerations, with a pulse structured according to the present invention it is possible to eliminate the drawbacks of prior art and significantly increase the results on treated tissue. In particular, the D-type pulse defined above enables plasma mediated ablation to be combined with laser ablation.

As plasma is photo-absorbent and reduces the ablation efficiency of the laser, the ideal fluences to obtain "cold" laser ablation vary in the interval of 4-19 J/cm$^2$. Acting with fluences in this interval, 20-40 μm of tissue per pulse is removed. In the D-type pulse, a series of hypo-energy sub-pulses Si (4-19 J/cm$^2$) forming the tail of the composite pulse, is preceded by a single hyper-energy pulse (40 J/cm$^2$) (pre-pulse Pi) capable of generating plasma to remove the epidermis but not such as to interact with the middle layers of the dermis. The hyper-energy pre-pulse Pi is then followed by a train of ablative hypo-energy laser pulses or laser sub-pulses Si, capable of generating "cold" ablation, but also of efficaciously inducing the hyperemia and shrinking effects of the collagen fibers located in the deep levels of the dermis.

According to some embodiments the D-type composite pulse is designed by a hyper-energy body or pre-pulse Pi which, according to the curves elaborated by Green (FIG. 17), is capable of generating only plasma. This pre-pulse Pi is followed immediately by a tail of sub-pulses Si, i.e. small hypo-energy pulses. In some embodiments the hyper-energy pre-pulse is characterized by an energy of 15 mJ, by an on-time τ-on of 60 μs, by a peak power of 250 W, by a spot (i.e. a circular area of incidence on the skin) with a diameter of 200 μm and consequently by an energy per unit of surface area of 47.7 J/cm$^2$. The subsequent sub-pulses Si can be characterized by an energy per pulse of 3 mJ, by an on-interval of 24 μs, by a peak power again equal to 250 W, by a spot diameter of 200 μm and consequently by an energy per unit of surface area of 9.5 J/cm$^2$.

The concept underlying the invention relates in general to implementation of a technology which is the result of combining different technologies with one another, in virtue of the knowledge of the various physical-biological phenomena taking place, according to precise relations of proportionality, both time- and space-related.

In this regard, again within the scope of regenerating and rejuvenating cosmetic treatments or of treatment for disfiguring scarring, it would also be possible to combine medical products, such as gels containing growth factors or biostimulating pharmaceutical products, with fractional technology. The limit of conventional fractional technology consists in the chemical-physical characteristics of lateral thermal damage induced by laser ablation not mediated by plasma. In fact, in these conditions the residual tissue is subject to hyalinization phenomena and represents an obstacle to the diffusion of the aforesaid products applied to the epidermis after laser treatment.

These limits are overcome by the use of an S-type pulse as defined above. As indicated above, the S-type pulse comprises a series of sub-pulses, for example characterized by a spot diameter of 150 μm and by an energy per unit of surface area comprised between 1 and 35 J/cm$^2$, for example comprised between 2 and 20 J/cm$^2$, preferably between 2 and 15 J/cm$^2$. These sub-pulses are therefore characterized by energies just above the threshold for significant plasma formation. In fact, plasma is photoabsorbent and therefore it would be counter-productive to emit energy per pulse greatly above this threshold. At these fluences the percentage of pulses forming plasma is significant and, according to Green (1990), is around 30%. A pulse thus obtained, as can be observed in the histologies, induces the formation of a hemispherical shaped crater. The main characteristic, which can be observed histologically, is that this crater is "clean", with negligible thermal damage and optimal elasticity both of the margins and of the edges of the cavity. All this can contribute to make the cavity extremely receptive to the application of optional medicated products.

Characteristics of the RF Current

As described with reference to FIGS. 6 and 7, the optical radiation generated by the laser source can be combined with the application of radiofrequency current through at least one electrode. The electrode is preferably integral with the same handpiece on which the laser emitter is located. Although a second electrode for closing the electrical circuit can also be provided, to be applied at a distance from the first, for example as an electrode to be placed in connection with a limb of the subject to which the treatment is applied, to obtain a concentration of the currents in the zone of the tissue to be treated, which is located in the zone of incidence of the laser beam, it is preferable to use two electrodes placed close to each other, preferably both carried by the same handpiece that also carries the laser emitter. In some embodiments, as shown in FIG. 6, the electrodes are adjacent to the zone irradiated by the laser source.

In some embodiments the radiofrequency current has a frequency comprised between 50 and 1000 kHz and preferably between 100 and 700 kHz. In currently preferred embodiments the frequency of the current is comprised between 400 and 600 kHz and even more preferably between 450 and 550 kHz. Application of the radiofrequency current can normally have a duration that is longer than the laser radiation application time. Typically, the emitting time of the radiofrequency current is comprised between 1 and 10 seconds. In preferred embodiments, the application time is comprised between 2 and 5 seconds. For reasons that will be apparent below, emission of the radiofrequency current does not start before application of the optical radiation by the laser source. Preferably, application of the laser radiation starts before application of the radiofrequency current. In some embodiments, emission of laser radiation stops before application of the radiofrequency current starts. In fact, the synergistic effect between the application of the two energy forms is presumably achieved as a result of the changes induced by the laser on the vascularized tissue, said changes facilitating the subsequent flow of radiofrequency electrical current in the volume of the tissue in which the application of this energy is required.

The power of the current emitted can advantageously be comprised between 5 and 100 W. In preferred embodiments the power is comprised between 10 and 50 W.

Combination of two different energy forms (optical and RF current), appropriately combined with each other in time and space, enables deep transfer of the quantity of energy capable of exceeding the activation threshold of the biological processes typical of tissue repair. The energy applied in the form of radiofrequency current emitted separately would not be capable of activating any biological process. At the same time, unless extremely invasive parameters (stack 3-5) are used, laser radiation alone would not be capable of reaching the reticular dermis in a quantity sufficient to significantly activate these processes.

Particularly advantageous embodiments of the invention provide for symbiotic energy combination so as to obtain a synergistic biological effect of the two energy forms, optical (laser) and electric (radiofrequency current). In other words, this combined emission of different energies, optical and RF current, gives rise to greater biological effects than the simple sum of the single energies emitted. Therefore, the time relationship between the single elements involved is important.

With reference to the rationale of the origin of the D-pulse, comprising a plasma ablation hyper-energy pre-pulse followed by a train of hypo-energy sub-pulses with laser-ablation effect, it can be observed that the RF current flows from the intact epidermis, due to the heat wave of the proximal portion of the ablation cavity generated by the plasma, to the ablation cavity generated by the laser pulse and from here jumps easily into the dilated capillaries that surround said cavity (see FIG. 12C).

The current jump directly from the epidermis to the surface capillaries is more difficult as these are located at about a hundred micrometers from the healthy epidermis and from the ablation cavity generated by the plasma. The sequence of the phenomena, laser ablation and RF current application, is very important for optimizing the phenomenon.

The application sequence, i.e. the time relations between the energies involved, plays an important role in the combination of the two energy forms. According to a possible interpretation of the action mechanism of the two energy forms applied, which is indicated here to provide an explanation of the synergistic effects obtained with the invention, but which must not be considered limiting, there is a close correlation between the two energies, dependent on concatenation of the biological events caused by them, which cannot be neglected to obtain a high treatment efficiency. The loss of efficiency could result in an unbalanced or excessive energy emission, which goes against the principles that inspire fractional technology with RF.

Figure 18:
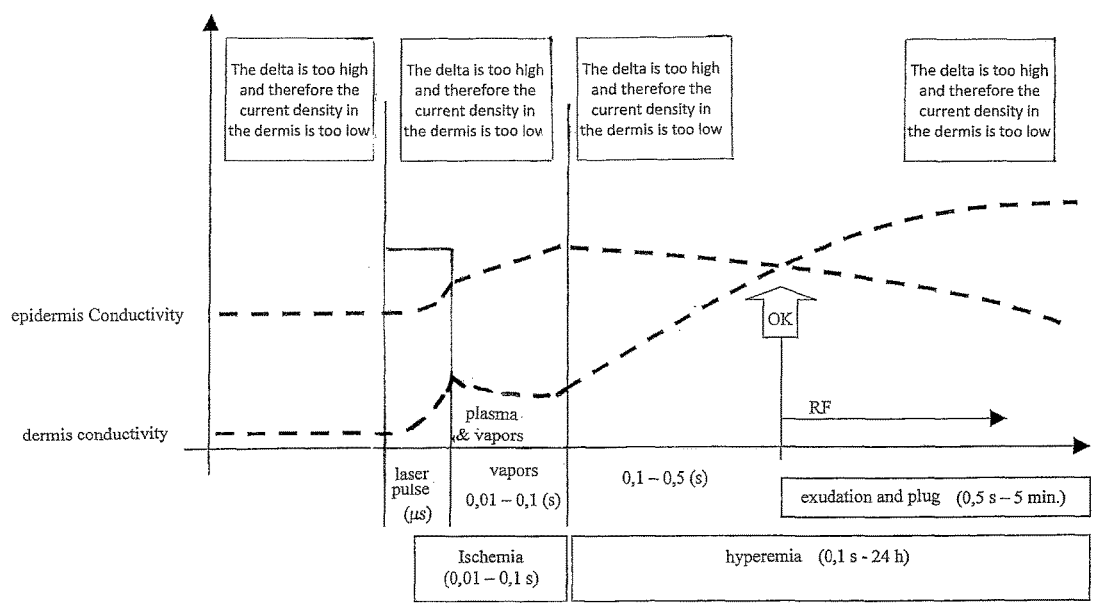
FIG. 18 shows a time diagram explaining the biological phenomena provoked by the combined application of optical energy in the form of laser radiation and electrical energy in the form of radiofrequency current.

According to a possible interpretation of the phenomena caused by combined emission of the two energy forms, which is provided here as possible explanation, but which the concepts underlying the invention are not bound to or dependent on, after laser ablation (mediated or not by plasma) a transitory ischemia followed by persistent hyperemia occurs, as represented schematically in FIG. 18.

In the diagram of FIG. 18 the time is indicated in the abscissa. As shown in the figure, the laser pulse is followed by a formation of vapors and plasma and by an ischemia of the tissue in the time interval from 0.01 to 0.1 seconds after the rising front of the pulse (in the case of composite pulses such as those described here, this is intended as the rising front of the pre-pulse in the case of composite D-type pulse, or the rising front of the first sub-pulse in the case of composite S-type pulse).

In the subsequent 24 hours there is an intense hyperemia of the tissue. Moreover, after the first half second, intense exudation takes place and plugs of exudate and keratin (crusts) form. The diagram shows the trends over time of the conductivity of the epidermis and of the dermis. As indicated in the diagram, it can be observed that the conductivity of the epidermis is generally greater than that of the dermis up to an instant (from a few tenths up to more than one second from the start of application of the laser pulse), in which the conductivity values are inverted, with the dermis that becomes more conductive than the epidermis. The instant in time in which the two curves cross over is the optimal moment for starting application of the energy in the form of RF current. Typically, the radiofrequency current can be applied starting from 0.8-1.2 seconds after the rising front of the laser pulse.

In fact, in the preceding instants there is an excessive gap in the conductivity between epidermis and dermis. To obtain a significant therapeutic effect, this impedance jump imposes the application of very high quantities of RF current, greater than those sufficient if the current is emitted starting from the cross-over point of the aforesaid electrical conductivity curves.

In this regard, to induce homogeneous hyperemia of the capillaries of the papillary dermis, the distribution in space of the heat waves generated by the laser radiation assumes considerable importance. In fact, it is important that the spots are distributed with the greatest possible distance between them, although still capable of ensuring a certain degree of overlapping of the heat fronts of the dermis. This ensures that all the capillaries will be involved by the phenomenon of vasodilation and the current can thus flow adequately through them to the reticular dermis.

Effects of the New Laser Pulses, Optionally in Combination with RF Current

Numerous clinical studies have been carried out to evaluate the effects of the new shapes of laser pulses described above, separately or combined with the application of radiofrequency current, in order to highlight their multiple ameliorative aspects over the prior art.

Typical applications relate to aesthetic treatments of the skin, in particular with the object of obtaining a reduction of wrinkles, firming and overall rejuvenation of the tissue.

In order to evaluate the different effects on tissue of the laser pulses SP and DP described above, in vivo tests were carried out on a sheep.

FIGS. 10A-10K show a selection of the results attained. Each figure indicates the type of pulse used (DP or SP), the duty cycle of the composite pulse, indicated as "burst" and expressed in percentage, the energy emitted per pulse expressed in mJ and the duration in microseconds of the composite pulse applied.

The microphotographs illustrated in FIGS. 10A-10K, in particular, show the effect of tissue ablation at the axis of the optical laser beam applied and the shrinkage effect. As can be observed from the histologies in all the photographs indicated in FIGS. 10A-10K, the SP pulse and the DP pulse differ considerably as far as the shape of the ablation zone, and shrinkage effect in the tissue surrounding the central zone involved, by laser beam, are concerned. The subsequent FIGS. 11A and 11B show a schematic representation of the ablation and shrinkage effect obtained respectively with the SP pulse (FIG. 11A) and with the DP pulse (FIG. 11B). FIGS. 12A and 12B schematically show the heat bubble that is generated in the tissue in the two cases (FIG. 12A for the SP pulse; FIG. 12B for the DP pulse).

Figure 10:
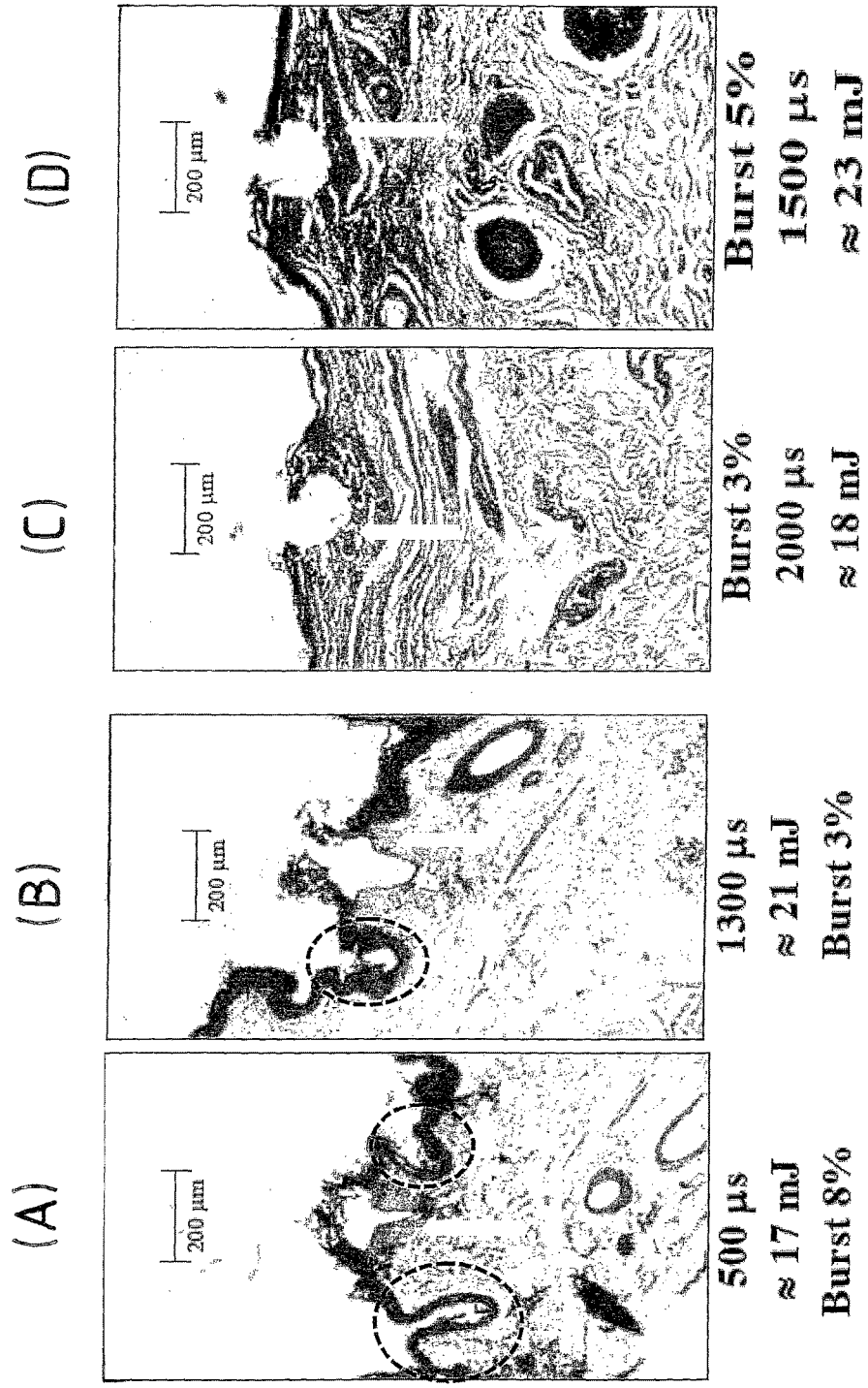
FIGS. 10A-10K show histological images of tissues treated with two different types of laser pulses according to the invention in different application conditions.
Figure 12:
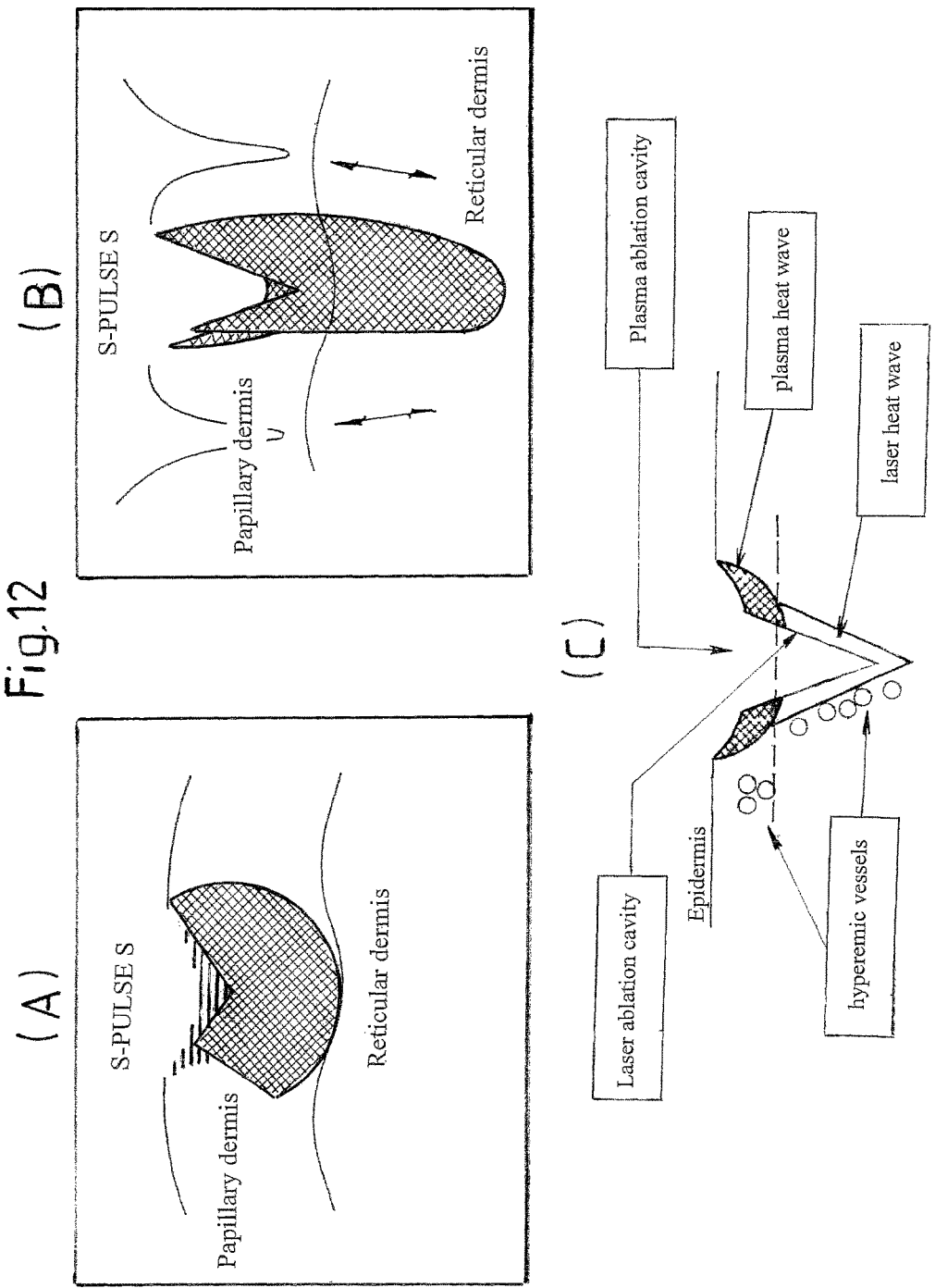

As can be observed from FIGS. 10-12, the SP pulse generates an ablation zone in the papillary dermis (PD) with modest shrinkage effect, while the DP pulse generates an ablation zone, again limited to the layer of papillary dermis (PD), but much deeper. The ablation zone is surrounded by a surrounding area in which the papillary dermis has undergone substantial contraction or shrinkage. From the viewpoint of heat (FIGS. 12A and 12B), it can be observed that the SP pulse generates a heat bubble, i.e. a thermal heating front of the tissue, which involves the thickness of the papillary dermis and laps the reticular dermis RD below. The DP pulse, characterized by the pre-pulse and by the tail formed by a sequence of high frequency sub-pulses, generates a heat bubble, i.e. a heat front represented in FIG. 12B, which besides passing through the papillary dermis also deeply penetrates the reticular dermis below.

FIG. 12C schematically shows the effect of ablation of the optical radiation in the two modes: direct laser ablation and plasma mediated ablation. The first cavity excavated in the epidermis is generated by plasma mediated ablation (indicated as "plasma ablation cavity" in the figure). The deepest part of the ablation (indicated as "laser ablation cavity" in the figure) is obtained by direct ablation using the laser beam. The figure also shows the zones involved by the heat wave generated by plasma and by the heat wave generated by laser radiation. As can be observed, the zone hit by the heat generated during the laser ablation phase (not plasma mediated) is located at a greater depth from the epidermis and penetrates the tissue in which there is greater density of blood vessels, which as a result of the radiation undergo dilation and hyperemia.

The effect of this increased penetration is an intense stimulation of the blood supply and consequently intense hyperemia of the tissue. Thermal stimulation of the reticular dermis also causes increased shrinkage of the surface layers of the papillary dermis.

The results illustrated above refer to applications of laser energy alone. The combination of laser radiation (emitted in the form of composite DP-type or SP-type pulses) with the emission of radiofrequency electrical current makes it possible to obtain an improvement of the treatment effects.

Penetration of the radiofrequency current in the tissue depends on the frequency of the current applied, on the magnetic permeability of the tissue and on the conductivity of the tissue according to the formula:

$$\delta = \frac{1}{\sqrt{\pi f \mu \sigma}}$$

where:
δ is the standard penetration depth expressed in m
$\pi = 3.14$
f is the frequency in Hz
μ is the magnetic permeability expressed in Henry per meter
σ is the electrical conductivity expressed in Siemens per meter.

FIG. 13 shows the trend of the electrical conductivity (expressed in S/m) as a function of the frequency of the current for the following tissues or structures:
BV: blood vessels
WS: wet skin
F: adipose tissue
DS: dry skin It can be observed in the diagram of FIG. 13 that the maximum conductivity is that of the blood vessels.

In the absence of ablation treatment and of vasodilation, the radiofrequency current flows for about 90% through the epidermis and only for 10% along the blood vessels. Following stimulation of the tissue by laser irradiation and above all as a result of ablation resulting from irradiation of the epidermis with the laser pulses, a substantial improvement of the radiofrequency current flow conditions is obtained.

Vasodilatation is mainly due to two effects: a first immediate effect is heating due to the heat wave. Heating of the blood vessels causes immediate vasodilation as a result of thermal effect. A second slower and more persistent effect is due to the action of the laser on neuro-modulating factors. This effect occurs with a delay compared to the first and has greater persistence over time.

Regardless of which of the two effects are used, vasodilation contributes to an increased flow of current through the blood vessels and consequent reduction in the flow of current in the surface layers (epidermis) of the skin. This is due both to the decrease in the distance between vessel walls and outer surface of the epidermis, and to the increased cross section of the vessel. Moreover, the formation of ablation cavities reduces locally, i.e. at the micro-hole obtained by the laser ablation effect on the tissue, the distance between outer surface of the epidermis and blood vessels. This enables more efficient deep penetration of the radiofrequency current. The formation of plasma in the ablation cavity, resulting from the localized increase in temperature caused by the laser, further improves electrical transmission.

Typically, from a distribution of 90% of current on the surface and 10% in the blood vessels, a distribution of around 60% of the radiofrequency current flowing at the level of the epidermis and 40% at the level of the blood vessels can be obtained as a result of the application of laser energy.

This increased flow of electrical current in the deep tissues causes deep hyperemia. This deep hyperemia in turn supplies the hyperemia of more superficial tissue, even after emission of energy from the outside has ceased.

The quantity of hemoglobin provides an indication of the level of tissue hyperemia. FIGS. 14A to 14E show diagrams of the trend of the variation in percentage of hemoglobin over time following treatment with laser or with laser and radiofrequency current according to the invention. The diagrams highlight the different effect of the various types of treatment with one or other of the two SP and DP pulses described above, with or without the application of radiofrequency current. The trend over time of the percentage of hemoglobin is indicative of the trend over time of the hyperemia. With an increase in blood flow, and consequently of hyperemia, there is an increase in hemoglobin. The abscissa indicates the time (not in scale) from the treatment and the ordinate indicates the variation in the percentage of hemoglobin starting from a base value corresponding to the origin of the ordinate (hemoglobin content before the treatment).

The parameters used to obtain the results indicated in these figures are the following:
average pulse power: 30 W
peak power: 250 W
D-pulse with pre-pulse Pi of 60 microseconds followed by 40 sub-pulses Si;
S-pulse with 40 sub-pulses
Stack 1 (one composite pulse)
Dwell time 1 ms
Energy per pulse 0.75 mJ
Radiofrequency energy: 30 W for 3 seconds at 500 kHz.

More in particular, FIG. 14A indicates two curves, marked with SP and DP, which show the trend of the variation of hemoglobin percentage over time following treatment with laser alone with SP-type pulses and with DP-type pulses respectively, without the application of radiofrequency current. It can be observed that in both cases the quantity of hemoglobin increases following the treatment and has a peak at around 18-20 hours after the treatment. However, in the case of treatment with DP-type pulse, the peak is much lower. In practice, this corresponds to a lower impact of the cosmetic treatment on the patient and consequently fewer negative side effects, such as reddening and swelling.

After passing the hyperemia peak within 24 hours from application, the hemoglobin values drop to levels that exceed the base values (pre-application) by less than 40%. However, it is noted that in the long term, more than 72 hours after the treatment, the hyperemia caused by treatment with DP-type pulses tends to remain above the base value, increasing slightly, while hyperemia caused by conventional pulses tends to decrease, returning toward the pre-application value.

In practice, this means that the treatment with DP pulses is less invasive, causing fewer undesirable side effects in the short time, but maintains the level of hyperemia at values above normal for longer times. This enables a longer lasting effect of stimulation of the biological processes that lead to the desired results of rejuvenation and toning of the tissue.

FIG. 14B compares the effects on the percentage content of hemoglobin obtained by the application of laser energy with SP pulse (SP curve) with those obtained by the combined application of laser pulses of SP-type and radiofrequency current.

It can be observed that by applying radiofrequency in combination with the SP-type pulse, there is a further reduction of the peak of increase of hyperemia. Therefore, an advantage of reduction of side effects is obtained in the short term (around 24 hours from application).

In the long term (over 72 hours) an increased hemoglobin content is observed, which indicates an increased degree of hyperemia over time, in the case of combined laser+RF treatment. This corresponds to the fact that the energy emitted through radiofrequency caused a deeper hyperemia, as the vasodilation caused by pre-treatment with the laser promoted the flow of electrical current in the deeper layers of the tissue, to the detriment of the flow in the outer layers of the epidermis. The deep hyperemia thus induced maintains a longer lasting effect over time, although reducing the hyperemia peak in the short term.

FIG. 14C compares the effect, in terms of variation of the percentage of hemoglobin content, of the laser beam with DP pulses alone (DP curve) and of the laser beam with DP pulses in combination with radiofrequency (DP+RF curve). It can be observed that the hyperemia peak in the 24 hours remains substantially unvaried, i.e. it is not influenced either positively or negatively by the combined application of laser energy and radiofrequency electrical energy. In the long term, a minimum is reached followed by an increase in both cases, with a steeper trend in the case of combined application.

The curves DP+RF and SP+RF of FIG. 14D show the trend of the variations of hemoglobin percentage over time in the case of combined application of laser+RF current in the two cases of SP pulse (SP+RF curve) and of DP pulse (DP+RF curve).

Finally, FIG. 14E shows overlapping of the four curves SP, DP, SP+RF, DP+RF. An ideal curve Id, indicated with a dashed line, is overlapped on these four curves; this represents the ideal trend that the hyperemia should have to obtain minimum undesirable side effects and maximum treatment efficacy. It can be observed that the use of a DP pulse, or the combined use of one of the two DP or SP pulses with the application of radiofrequency current provides hyperemia curves which are closer to the ideal curve and therefore more favorable. In particular, it can be observed that the shape of the DP pulse enables, even without the application of radiofrequency current, a particularly efficient result to be obtained in terms of trend over time of the hyperemia.

A hyperemia that lasts over time enables more efficient tissue repair to be obtained as a result of the effect of the hyperemia on pH values, temperature, NO, $ptO_2$, $ptCO_2$, $O_2$, activation of cellular redox complexes, acute phase proteins, cytokines, cellular proliferation speed, cellular differentiation and cellular renewal speed.

Besides the effects in terms of inducing hyperemia, and the trend over time thereof, another important factor in evaluating the efficacy of these treatments is the shrinkage effect on tissue and in particular on collagen. Shrinkage is an effect of considerable importance in treatments to rejuvenate the epidermis, reduce wrinkles, and to tone and firm tissue.

Tests performed using the various combinations of pulses SP, DP and SP+RF, DP+RF gave results that are variable as a function of the type of treatment carried out. The degree of shrinkage can be determined simply by measuring the distance between points of the treatment pattern at the time of application and in a time interval subsequent to application. FIG. 15 indicates in the ordinate the average distance between the points of the pattern, i.e. the average distance between the centers of the marks of the laser beam for the four possible combinations indicated in the abscissa:

SP: laser alone with SP pulse
DP: laser alone with DP pulse
SP+RF: laser with SP pulse in combination with radiofrequency current;
DP+RF: laser with DP pulse in combination with radiofrequency current.

The diagram indicates squares labelled Im and 120. The former indicate the values immediately after treatment, i.e. indicative of the shrinkage obtained as an immediate effect of the treatment on the tissue. The squares indicated with 120 indicate data collected 120 hours after treatment. The statistical significance of the data is marked with (***) (=significance greater than 99%) and ns (statistically insignificant data).

In the diagram of FIG. 15 it can be observed that in the long term the effect in terms of shrinkage is greater in the case of combined laser+radiofrequency treatment, regardless of the type of laser pulse (SP, DP) used.

The excellence of the treatment is also determined as a function of the time required for complete recovery of the subject treated, i.e. the time necessary for the traces of the treatment to disappear from the epidermis. The experimental results relating to this aspect are summed up in the diagram of FIG. 16.

In this diagram the abscissa indicates the time expressed in days since treatment (origin of the abscissa). The ordinate indicates the percentage of plugs of exudate and keratin, hereinafter improperly called "crusts", which persist over time. Immediately after the treatment 100% of the crusts are visible. The four curves indicated with DP+RF, SP+RF, DP and SP show the trend over time of the reduction in the number of crusts. It can be observed in the graph that the treatment with laser alone and SP pulse causes greater persistence of these crusts, while combined treatment of laser radiation with DP-type pulse and radiofrequency current is characterized by a substantial decrease in the time required for the disappearance of a high percentage (80%) of the crusts. In the case of treatment with DP pulses and radiofrequency, over 80% of the crusts had already disappeared 8-9 days after treatment, while in the case of application of laser alone with SP pulses the same level of decrease is only reached 13 days after treatment.

While the embodiments described of the object illustrated here have been shown in the drawings and described in full in the above with particulars and details in relation to the different examples of embodiment, those skilled in the art will understand that a number of modifications, changes and omissions are possible without departing from the innovative teachings, from the principles and from the concepts set forth above, and from the advantages of the object defined in the appended claims. Therefore, the effective scope of the innovations described must be determined only on the basis of the widest interpretation of the appended claims, so as to comprise all modifications, changes and omissions. In addition, the order or sequence or any step of the method or process can be varied or rearranged according to alternative embodiments. In particular, it is possible to obtain the above-described synergistic effects from combination of the laser radiation and of the radiofrequency current also using other shapes of laser pulse, such as a sequence of simple pulses, with appropriate repetition frequency.

DIDASCALIE FIGURE

FIG. 8 e FIG. 9: Peak power/Stay time

FIG. 11 e 12 (A) e (B): PULSE S/Papillary dermis/reticular dermis

FIG. 12 (C): Laser ablation cavity/plasma ablation cavity/epidermis/hyperemic vessels/plasma heat wave/laser heat wave FIG. 13: Conductivity/Frequency FIG. 14: hours FIG. 15: Shrinkage FIG. 16: days FIG. 17: Plasma formation FIG. 18: the delta is too high and therefore the current density in the dermis is too low/Conductivity epidermis/conductivity dermis/plasma & vapors/laser pulse/vapors/exudation and plug/ischemia/hyperemia

The invention claimed is:

1. A system for treating a region of the epidermis, the system comprising:
at least one laser energy source;
a time control device configured to generate a laser beam comprising a plurality of composite pulses, each of said composite pulses being emitted at a base frequency, each of said composite pulses comprising a sequence of sub-pulses, said sequence of sub-pulses being emitted at a frequency that is higher than said base frequency, each of said composite pulses comprising a first interval of continuous pre-pulse emission followed by a sub-pulse sequence emission interval, said sub-pulse sequence emission interval comprising a train of sub-pulses following said pre-pulse emission, said first interval of continuous pre-pulse emission comprising a first interval pre-pulse emission duration, each of said subsequent sub-pulses having a sub-pulse duration, said first interval pre-pulse emission duration being greater than said sub-pulse duration of each of said sub-pulses;
a laser energy focusing system arranged and configured to direct said laser beam on said region of the epidermis.

2. The system according to claim 1, wherein said base frequency is comprised between 1 and 1090 Hz.

3. The system according to claim 1, wherein said composite pulse comprises a pre-pulse with a higher energy per surface unit than said sub-pulses.

4. The system according to claim 1, wherein said pre-pulse emission has a higher peak power than a peak power of the subsequent sub-pulses.

5. The system according to claim 1, wherein said laser energy focusing system is arranged and controlled to treat contiguous volumes of the epidermis distributed according to a pattern, wherein each volume treated has a center substantially positioned on an axis of the laser beam used to treat said volume, wherein axes of laser beams used to treat said contiguous volumes are distributed according to a presettable matrix of points.

6. The system according to claim 5, wherein said focusing system is arranged and designed to direct one or more laser beams according to pitches spaced from one another from 50 micrometers to 1000 micrometers.

7. The system according to claim 1, further comprising a radio frequency current source and at least one electrode for applying a radio frequency current.

8. The system according to claim 7, further comprising another electrode to provide two electrodes for applying the radiofrequency current.

9. The system according to claim 7, wherein said radiofrequency current source and said at least one laser energy source are controlled so as to apply a radiofrequency current generated by said radio frequency current source coordinated in time with application of said laser beam.

10. The system according to claim 9, wherein said radiofrequency current source and said at least one laser energy source are coordinated in time so as to apply a radiofrequency current at least partly simultaneously to, and/or in a sequence with, the application of said laser beam.

11. The system according to claim 7, wherein said radiofrequency current source is controlled to apply a radiofrequency current for a time comprised between 1 and 10 seconds, on a portion of epidermis, in combination with application of said laser beam.

12. The system according to claim 7, wherein said radiofrequency current source generates a current at a frequency comprised between 50 and 1000 kHz.

13. The system according to claim 7, wherein said radiofrequency current source applies a power comprised between 5 and 100 W.

14. The system according to claim 7, wherein said radiofrequency current source is controlled to start to emit with a time delay from 0.1 to 1.5 seconds from a start of laser emission.

15. The system according to claim 7, wherein said at least one electrode comprises a means for reducing or preventing formation of electric discharges between the at least one electrode and a tissue to be treated.

16. The system according to claim 1, wherein said at least one laser energy source has a wavelength comprised between 532 and 13,000 nm.

17. The system according to claim 16, wherein said at least one laser energy source is a CO2 laser with emission at 10600 nm.

18. The system according to claim 1, further comprising a scanning device to direct said laser beam on multiple points of a portion of epidermis to be treated, spaced from one another.

19. The system according to claim 1, further comprising a waveguide to convey laser energy from said at least one laser energy source towards an applicator handpiece.

20. The system according to claim 19, further comprising a scanning device to direct said laser beam on multiple points of epidermis to be treated, spaced from one another, wherein said scanning device is housed in said applicator handpiece.

21. The system according to claim 7, further comprising a waveguide to convey laser energy from said at least one laser energy source towards an applicator handpiece, wherein said at least one electrode for applying radiofrequency current is carried by said handpiece.

22. The system according to claim 8, wherein said handpiece carries said two electrodes for applying radiofrequency current.

23. The system according to claim 2, wherein said composite pulse comprises a pre-pulse with a higher energy per surface unit than said sub-pulses.

24. The system according to claim 2, wherein said pre-pulse emission has a higher peak power than a peak power of the subsequent sub-pulses.

25. The system according to claim 3, wherein said pre-pulse has a higher peak power than a peak power of the subsequent sub-pulses.

26. The system according to claim 5, wherein said focusing system is arranged and designed to direct one or more laser beams according to pitches spaced from one another from 90 to 550 micrometers.

27. The system according to claim 7, wherein said radiofrequency current source is controlled to apply a radiofrequency current for a time comprised between 2 and 5 seconds on a portion of epidermis, in combination with application of said laser beam.

28. The system according to claim 7, wherein said radiofrequency current source generates a current at a frequency comprised between 100 and 700 kHz.

29. The system according to claim 7, wherein said radiofrequency current source generates a current at a frequency comprised between 400 and 600 kHz.

30. The system according to claim 7, wherein said radiofrequency current source generates a current at a frequency comprised between 450 and 550 kHz.

31. The system according to claim 7, wherein said radiofrequency current source applies a power comprised between 10 and 50 W.

32. A system for treating a region of the epidermis, the system comprising:
   a laser energy source;
   a time control device configured to generate a laser beam comprising a plurality of composite pulses emitted at a base frequency, each of said composite pulses comprising a sequence of sub-pulses, said sequence of sub-pulses being emitted at a higher frequency than said base frequency, each of said composite pulses comprising a first interval of continuous pre-pulse emission followed by a sub-pulse sequence emission interval, said sub-pulse sequence emission interval comprising a plurality of sub-pulses following said pre-pulse emission, said first interval of continuous pre-pulse emission having a greater duration than each of said subsequent sub-pulses;
   a laser energy focusing system configured to direct said laser beam on said region of the epidermis.

33. The system according to claim 32, wherein said base frequency is comprised between 1 and 1090 Hz.

34. The system according to claim 32, wherein said composite pulse comprises a pre-pulse with a higher energy per surface unit than said sub-pulses.

35. The system according to claim 32, wherein said pre-pulse emission has a higher peak power than a peak power of the subsequent sub-pulses.

36. A system for treating a region of the epidermis, the system comprising:
   a laser energy source;
   a time control device configured to generate a laser beam, said laser beam comprising a plurality of composite pulses emitted at a base frequency, each of said composite pulses comprising a continuous pre-pulse emission interval followed by a sub-pulse sequence emission interval, said continuous pre-pulse emission interval comprising a continuous pre-pulse emission, said sub-pulse sequence emission interval comprising a plurality of sub-pulses following said pre-pulse emission, said continuous pre-pulse emission interval comprising a pre-pulse emission interval duration, each of said sub-pulses comprising a sub-pulse duration, said pre-pulse emission interval duration being greater than said sub-pulse duration of each of said sub-pulses, said plurality of sub-pulses being emitted at a sub-pulse frequency, said sub-pulse frequency being greater than said base frequency,
   a laser energy focusing system configured to direct said laser beam on said region of the epidermis.

* * * * *